US010393731B2

(12) United States Patent
Ignoni et al.

(10) Patent No.: US 10,393,731 B2
(45) Date of Patent: Aug. 27, 2019

(54) CELLULAR-BASED METHOD FOR DETERMINING THE BIOLOGICAL ACTIVITY OF DEFIBROTIDE

(71) Applicant: GENTIUM S.R.L., Villa Guardia (CO) (IT)

(72) Inventors: Terenzio Ignoni, San Fermo Della Battaglia (IT); Vijay Kumar, Casnate (IT); Claudio Verga, Bregnano (IT)

(73) Assignee: GENTIUM S.R.L., Villa Guardia (CO) (IT)

( * ) Notice: Subject to any disclaimer, the term of this patent is extended or adjusted under 35 U.S.C. 154(b) by 0 days.

(21) Appl. No.: 15/529,814

(22) PCT Filed: Nov. 23, 2015

(86) PCT No.: PCT/EP2015/077355
§ 371 (c)(1),
(2) Date: May 25, 2017

(87) PCT Pub. No.: WO2016/083297
PCT Pub. Date: Jun. 2, 2016

(65) Prior Publication Data
US 2017/0322199 A1 Nov. 9, 2017

(30) Foreign Application Priority Data

Nov. 27, 2014 (EP) .................................... 14195277

(51) Int. Cl.
*G01N 33/50* (2006.01)
(52) U.S. Cl.
CPC ..... *G01N 33/5014* (2013.01); *G01N 33/5064* (2013.01)
(58) Field of Classification Search
CPC .................................................. G01N 33/5064
See application file for complete search history.

(56) References Cited

U.S. PATENT DOCUMENTS

| 3,770,720 | A | 11/1973 | Butti et al. |
| 3,829,567 | A | 8/1974 | Butti et al. |
| 3,899,481 | A | 8/1975 | Butti et al. |
| 4,234,682 | A | 11/1980 | Bartl et al. |
| 4,649,134 | A | 3/1987 | Bonomini |
| 4,693,995 | A | 9/1987 | Prino et al. |
| 4,694,134 | A | 9/1987 | Ross |
| 4,753,221 | A | 6/1988 | Kensey et al. |
| 4,853,221 | A | 8/1989 | Elslager |
| 4,985,552 | A | 1/1991 | Fedeli et al. |
| 5,081,109 | A | 1/1992 | Ulutin |
| 5,116,617 | A | 5/1992 | Mantovani et al. |
| 5,223,609 | A | 6/1993 | Fedeli et al. |
| 5,231,006 | A | 7/1993 | Kolde |
| 5,624,912 | A | 4/1997 | Burcoglu et al. |
| 5,646,127 | A | 7/1997 | Lanzarotti et al. |
| 5,646,268 | A | 7/1997 | Lanzarotti et al. |
| 5,856,444 | A | 1/1999 | Kawakita et al. |
| 5,919,772 | A | 7/1999 | Szyf et al. |
| 5,977,083 | A | 11/1999 | Burcoglu |
| 6,046,172 | A | 4/2000 | Ennio et al. |
| 6,573,372 | B2 | 6/2003 | McCall et al. |
| 6,699,985 | B2 | 3/2004 | Burcoglu |
| 7,338,777 | B2 | 3/2008 | Porta et al. |
| 7,785,797 | B2 | 8/2010 | Wohlgemuth et al. |
| 8,551,967 | B2 | 10/2013 | Ferro et al. |
| 8,980,862 | B2 | 3/2015 | Iacobelli |
| 9,539,277 | B2 | 1/2017 | Iacobelli |
| 2002/0142029 | A1 | 10/2002 | Porta et al. |
| 2003/0013669 | A1 | 1/2003 | Burcoglu |
| 2004/0131588 | A1 | 7/2004 | Ferro et al. |
| 2004/0248834 | A1 | 12/2004 | Klinman et al. |
| 2005/0009131 | A1 | 1/2005 | Porta et al. |
| 2005/0059629 | A1 | 3/2005 | Gaarde et al. |
| 2005/0196382 | A1 | 9/2005 | Vaillant et al. |
| 2005/0215498 | A1 | 9/2005 | Eissner et al. |
| 2007/0037144 | A1 | 2/2007 | Wohlgemuth et al. |
| 2009/0131362 | A1 | 5/2009 | Echart et al. |
| 2010/0254938 | A1 | 10/2010 | Ferro et al. |
| 2011/0092576 | A1 | 4/2011 | Stein et al. |
| 2012/0121698 | A1 | 5/2012 | Mehar et al. |
| 2013/0231470 | A1 | 9/2013 | Iacobelli |
| 2015/0176003 | A1 | 6/2015 | Ignoni et al. |
| 2015/0196580 | A1 | 7/2015 | Echart |
| 2015/0297624 | A1 | 10/2015 | Iacobelli |
| 2017/0080012 | A1 | 3/2017 | Iacobelli |

FOREIGN PATENT DOCUMENTS

| DE | 19740384 A1 | 3/1999 |
| EP | 0558833 A2 | 9/1993 |
| EP | 0937461 A1 | 8/1998 |

(Continued)

OTHER PUBLICATIONS

"Defibrotide—Substance Summary," SIDS 51091757, PubChem Substance, Retrieved from http://pubchem.ncbi.nlm.nih.gov on Mar. 11, 2009, 3 pages.
"Everything you ever wanted to know concerning Oligonucleotides but were afraid to ask," downloaded Jul. 9, 2010 from http://www.auburn.edu/.about.santosr/protocols/OligoProtocols.pdf, 5 pages.
Abdalla, S.A. et al., "Prognostic relevance of microvessel density in colorectal tumours," Oncology Reports, vol. 6, Apr. 16, 1999, pp. 839-842.
Akaogi, Jun, et al. "Role of PGE2 and EP Receptors in the Pathogenesis of Rheumatoid Arthritis and as a Novel Therapeutic Strategy." E Endocrine, Metabolic & Immune Disorders-Drug Targets (Formerly Current Drug Targets—Immune, Endocrine & Metabolic Disorders) (2006); 6(4): 383-394.

(Continued)

*Primary Examiner* — Bin Shen
(74) *Attorney, Agent, or Firm* — Cooley LLP

(57) ABSTRACT

The present invention relates to cell-based methods for determining the biological activity of defibrotide. In particular, the invention provides a method for assessing the potency of defibrotide by assessing the viability of mammalian cells in the presence of at least one cytotoxic agent and one or more concentrations of defibrotide. Such methods are particularly useful for standardizing pharmaceutical compositions comprising defibrotide.

20 Claims, 10 Drawing Sheets

(56) References Cited

FOREIGN PATENT DOCUMENTS

| | | |
|---|---|---|
| EP | 1059092 A1 | 12/2000 |
| EP | 1147777 A1 | 10/2001 |
| EP | 1325962 A1 | 7/2003 |
| EP | 1550462 A1 | 7/2005 |
| EP | 1276497 B1 | 11/2005 |
| EP | 1872787 A1 | 1/2008 |
| JP | H02-149527 A | 6/1990 |
| JP | H08-127539 A | 5/1996 |
| JP | 2005-527636 A | 9/2005 |
| WO | WO 1987/006235 A1 | 10/1987 |
| WO | WO 1992/021402 A1 | 12/1992 |
| WO | WO 1998/048843 A1 | 11/1998 |
| WO | WO 1998/054313 A2 | 12/1998 |
| WO | WO 1999/012935 A1 | 3/1999 |
| WO | WO 1999/057153 A1 | 11/1999 |
| WO | WO 2000/074634 A2 | 12/2000 |
| WO | WO 2001/078761 A2 | 10/2001 |
| WO | WO 2002/053700 A2 | 7/2002 |
| WO | WO 2003/004705 A1 | 1/2003 |
| WO | WO 2003/027313 A2 | 4/2003 |
| WO | WO 2003/052130 A2 | 6/2003 |
| WO | WO 2003/101468 A1 | 12/2003 |
| WO | WO 2004/003166 A2 | 1/2004 |
| WO | WO 2004/028516 A2 | 4/2004 |
| WO | WO 2004/078922 A2 | 9/2004 |
| WO | WO 2005/023273 A1 | 3/2005 |
| WO | WO 2006/094916 A1 | 9/2006 |
| WO | WO 2006/094917 A2 | 9/2006 |
| WO | WO 2006/119619 A1 | 11/2006 |
| WO | WO 2008/000549 A1 | 1/2008 |
| WO | WO 2008/125424 A1 | 10/2008 |
| WO | WO 2012/063272 A1 | 5/2012 |
| WO | WO 2013/190582 A1 | 12/2013 |
| WO | WO 2016/083297 A1 | 6/2016 |

OTHER PUBLICATIONS

Albini, A. et al., "A Rapid in Vitro Assay for Quantitating the Invasive Potential of Tumor Cells," American Association for Cancer Research, vol. 47, Jun. 15, 1987, pp. 3239-3245.

Algire, G., "An Adaptation of the Transparent-Chamber Technique to the Mouse," Journal of the National Cancer Institute, vol. 4, No. 1, Aug. 1943, 11 pages.

Andersen, N. F. et al., "Syndecan-1 and angiogenic cytokines in multiple myeloma: correlation with bone marrow angiogenesis and survival," British Journal of Haematology, 2004, vol. 128, pp. 210-217.

Arauz-Pacheco, C. et al., "The treatment of hypertension in adult patients with diabetes," Diabetes Care, vol. 25, No. 1, Jan. 2002, pp. 134-147.

Argoff, C.E. et al., "Diabetic Peripheral Neuropathic Pain: Clinical and Quality-of-Life Issues," Mayo Clinic Proceedings, Supplement, Apr. 2006, vol. 81, No. 4, 34 pages.

Becker et al., "Organikum: organisch-chemisches grundpraktikum" 1990, Deutscher Verlag der Wissenschaften, Berlin, with Google translation, 3 pages.

Belcaro, G. et al., "Fibrinolytic Enhancement in Diabetic Microangiopathy with Defibrotide," Angiology, The Journal of Vascular Diseases, vol. 43, No. 10, Oct. 1992, pp. 793-800.

Belcaro, G. et al., "Laser Doppler Flowmetry and Transcutaneous Oximet Evaluation in Microangiopathic Diabetic Patients Treated with Defibrotide," Current Therapeutic Research, vol. 46, No. 5, May 1989, pp. 726-732.

Benimetskaya et al., "Angiogenesis alteration by defibrotide: implications for its mechanism of action in severe hepatic veno-occlusive disease," Blood, vol. 112, No. 10, Nov. 15, 2008, pp. 4343-4352.

Berti, F. et al., "Effects of defibrotide on prostacyclin release from isolated rabbit kidneys and protection from post-ischemic acute renal failure in vivo," Eicosanoids, vol. 4, 1991, pp. 209-215.

Bianchi, G. et al., "Defibrotide, a Prostacyclin Releasing Agent, Protects the Rabbit Kidney from Acute Failure," Advances in Prostaglandin, Thromboxane, and Leukotriene Research, vol. 21, 1990, pp. 711-714.

Biedermann, B.C., "Vascular endothelium and graft-versus-host-disease," Best Practice & Research Clinical Haematology, vol. 21(2): 129-138, 2008.

Bonomini, V. et al., "Effect of a new antithrombotic agent (defibrotide) in acute renal failure due to thrombotic microangiopathy," Nephron, vol. 40, No. 2, 1985, pp. 195-200.

Bonomini, V. et al., "Use of Defibrotide in Renal Transplantation in Man," Haemostasis, vol. 16, Supp. 1, 1986, pp. 48-50.

Bostwick, D.G. et al., "Microvessel density in prostate cancer: prognostic and therapeutic utility," Seminars in Urologic Oncology, vol. 16, No. 3, Aug. 1998, pp. 118-123.

Brenchley, "Antagonising angiogenesis in rheumathoid arthritis," Annals of the Rheumatic Diseases, vol. 60, 2001, pp. 71-74.

Budavari, S. et al. (eds.), The Merck Index, Twelfth Edition, Merck & Co., Inc., Whitehouse Station, NJ, p. 484 (1996).

Burra, P. et al., "Warm Hepatic Ischemia in Pigs: Effects of L-Arginine and Oligotide Treatment," Journal of Investigative Surgery, vol. 14, 2001, pp. 303-312.

Cao, Y., "Tumor angiogenesis and therapy," Biomedicine & Pharmacotherapy, vol. 59, 2005, pp. S340-S343.

Carlo-Stella, C. et al. "Defibrotide significantly enhances peripheral blood progenitor cell mobilization induced by recombinant human granulocyte colony-stimulating factor (rhG-CSF)." Blood. vol. 96. No. 11. Abstract #2374, 2000, p. 553a, 2 pages.

Carlo-Stella, C. et al., "Defibrotide in Combination with Granulocyte Col Significantly Enhances the Mobilization of Primitive and Committed Perip Cells in Mice," Cancer Research, vol. 62, Nov. 1, 2002, pp. 6152-6157.

Chalandon, Y., et al., "Prevention of Veno-Occlusive Disease with Defibrotide after Allogeneic Stem Cell Transplantation." Biology of Blood and Marrow Transplantation (2004); 10: 347-354.

Chapter II Demand for related International Application No. PCT/EP2007/054633, dated Apr. 9, 2008, 10 pages.

Chopra et al., "Defibrotide for the treatment of hepatic veno-occlusive disease: results of the European compassionate-use study," British Journal of Haemoyology 111:1122-1129, 2000.

Coccheri et al. "Defibrotide," Cardiovascular Drug Reviews, vol. 9: 172-196, 1991.

Coccheri, S. et al., "Defibrotide as a Possible Anti-Ischemic Drug," Seminars in Thrombosis and Hemostasis, vol. 22, Supp. 1, 1996, pp. 9-14.

Comandella, M.G. et al., "Functional and morphological effects of defibrotide on renal ischemia," Research in Experimental Medicine, vol. 193, 1993, pp. 65-71.

Conde-Knape, K. et al., "Heparan sulfate proteoglycans in experimental models of diabetes: a role for perlecan in diabetes complications," Diabetes/Metabolism Research and Reviews, vol. 17, 2001, pp. 412-421.

Copelan, E.A. et al., "Hematopoietic Stem-Cell Transplantation," N Engl. J. Med. 354:17, Apr. 27, 2006, pp. 1813-1826.

Coppell, J.A. et al., "Hepatic Veno-Occlusive Disease following Stem Cell Transplantation: Incidence, Clinical Course, and Outcome," Biol. Blood Marrow Transplant (2010) 16, pp. 157-168.

Corbacioglu, S. et al., "Defibrotide for Prophylaxis of Hepatic Veno-Occlusive Disease in Paediatric Haemopoietic Stem-Cell Transplantation: An Open-Label, Phase 3, Randomised Controlled Trial," Lancet 379: 1301-1309, 2012.

Corsi, M. et al., "Antiischaemic effect of defibrotide treatment in rat kidney," Drugs Experimental Clinical Research, vol. 19, No. 6, 1993, pp. 261-265.

Corsi, M. et al., "Possible Role of Defibrotide in Endothelial Cell Protection," International Journal of Tissue Reactions, XV(4), 1993, pp. 157-161.

Craddock, C.F. et al., "Antibodies to VLA4 Integrin Mobilize Long-Term Repopulating Cells and Augment Cytokine-Induced Mobilization in Primates and Mice," Blood, vol. 90, No. 12, Dec. 15, 1997, pp. 4779-4788.

Davi, G. et al., "Effects of Defibrotide on Fibrinolytic Activity in Diabetic Patients with Stable Angina Pectoris," Thrombosis Research, vol. 65, No. 2, 1992, pp. 211-220.

Davis, S. "Insulin, Oral Hypoglycemic Agents, and the Pharmacology of the Endocrine Pancreas," Goodman and Gilman's The

(56) References Cited

OTHER PUBLICATIONS

Pharmacological Basis of Therapeutics, Chapter 60, Section XII, Hormone sand Hormone Antagonists, McGraw-Hill, 2006, pp. 1613-1645.
De Mestre, A.M. et al., "Regulation of Inducible Heparanase Gene Transcription in Activated T Cells by Early Growth Response 1," The Journal of Biological Chemistry, vol. 278, No. 50, Dec. 12, 2003, pp. 50377-50385.
Dempsey, L. et al., "Heparanase expression in invasive trophoblasts and acute vascular damage," Glycobiology, vol. 10, No. 5, 2000, pp. 467-475.
Denne, J.S., "Sample size recalculation using conditional power," Statist. Med. 2001; 20: pp. 2645-2660.
Dickerson, R.E. et al., "The Anatomy of A-, B- and Z-DNA," Science, vol. 216, No. 4545, 1982, pp. 475-485.
Dignan, F., et al., "Prophylactic defibrotide in allogeneic stem cell transplantation: minimal morbidity and zero mortality from veno-occlusive disease." Bone Marrow Transplantation (2007); 40: 79-82.
DrugBank, "Showing drug card for Defibrotide (DB04932)," retrieved Jan. 21, 2007 from http://www.drugbank.ca/cgi-bin/getCard.cgi?CARD=DB04932.txt, 10 pages.
Echart, C.L. et al., "The fibrinolytic mechanism of defibrotide: effect of defibrotide on plasmin activity," Blood Coagulation and Fibrinolysis 2009, vol. 20, No. 8, pp. 627-634.
Eissner, G. et al., "Defibrotide, a DNA-based drug, modulates endothelial cell function in multiple ways—impact for transplantation and cancer therapy," Vascular Pharmacoloby, vol. 45, No. 3, Sep. 1, 2006, pp. E152-E153.
Eissner, G. et al., "Fludarabine induces apoptosis, activation, and allogenicity in human endothelial and epithelial cells: protective effect of defibrotide," Blood, Jul. 1, 2002 vol. 100, No. 1, pp. 334-340.
Eissner, G. et al., "Oliogotide, a defibrotide derivative, protects human microvascular endothelial cells against fludarabine-induced activation, damage and allogenicity," Bone Marrow Transplantation, Mar. 2005, 35, pp. 915-920.
Ertault-Daneshpouy, M. et al., "Pericapillary hemorrhage as criterion of severe human digestive graft-versus-host disease," Blood, Jun. 15, 2004, vol. 103, No. 12, pp. 4681-4684.
Esau, Christine C. et al, "Therapeutic potential for microRNAs," Advanced Drug Delivery Reviews, vol. 59, 2007, pp. 101-114.
European Pharmacopoeia 5.0, 5.3 Statistical Analysis, pp. 475-504 (2005), 30 pages.
Falanga, A. et al., "Defibrotide reduces procoagulant activity and increases fibrinolytic properties of endothelial cells," Leukemia (2003);17(8):1636-1642.
Fernandez Pujol, B. et al., "Dendritic cells derived from peripheral monocytes express endothelial markers and in the presence of angiogenic growth factors differentiate into endothelial-like cells," European Journal of Cell Biology, vol. 80, Issue 1, 2001, pp. 99-110.
Ferrara, J.L.M. et al., "Graft-versus-host disease," Lancet 2009: vol. 373, May 2, 2009, pp. 1550-1561.
Ferrero, M.E. et al., "Efficacy of Defibrotide Treatment in Favoring the Function of the Grafted Heart and Kidney in Rats," Transplantation Proceedings, vol. 26, No. 1, Feb. 1994, pp. 251-252.
Ferrero, M.E. et al., "Prostacyclin Release from Endothelial Cells, Induced by Defibrotide Treatment, Favours the Function of Grafted Rat Hearts and Kidneys," International Journal of Tissue Reactions, XIII 4, 1991, pp. 215-218.
Folkman, J. et al., "Isolation of a tumor factor responsible for angiogenesis," Journal of Experimental Medicine, vol. 133, Issue 2, Feb. 1, 1971, pp. 275-288.
Folkman, J. et al., "Switch to the Angiogenic Phenotype during Tumorigenesis," Princess Takamatsu symposia, Jan. 1991, Boca Raton, pp. 339-347.
Fong, D.S. et al., "Diabetic Retinopathy," Diabetes Care, vol. 27, No. 10, Oct. 2004, pp. 2540-2553.
Fontanini, G. et al., "Microvessel count predicts metastatic disease and survival in non-small cell lung cancer," Journal of Pathology, vol. 177, 1995, pp. 57-63.
Frasca, G.M. et al., "Defibrotide Treatment and Disease Progression in Patients with IgA Nephropathy and Impaired Renal Function at Diagnosis," Clinical Drug Investigation, vol. 13, Issue 4, Apr. 1997, pp. 185-191.
Frasca, G.M. et al., "Effects of defibrotide treatment in patients with IgA nephropathy and reduced renal function," Nephrology Dialysis Transplantation, vol. 11, No. 2, 1996, pp. 392-393.
Friberger, P. et al., "Methods for determination of plasmin, antiplasmin and plasminogen by means of substrate S-2251," Haemostasis, 7:138-145 (1978).
Gharib et al., "Venous occlusive disease in children," Thrombosis Research, vol. 118: 27-38, 2006.
Giraud-Panis, M-J. et al., "Transplatin-modified oligonucleotides as modulators of gene expression," Pharmacology & Therapeutics, vol. 85, 2000, pp. 175-181.
Goldshmidt, O. et al., "Cell surface expression and secretion of heparanase markedly promote tumor angiogenesis and metastasis," Proceedings of the National Academy of Sciences, vol. 99, No. 15, Jul. 23, 2002, pp. 10031-10036.
Guba, M. et al., "Rapamycin induces tumor-specific thrombosis via tissue factor in the presence of VEGF," Blood, vol. 105, Jun. 1, 2005, pp. 4463-4469.
Guba, M. et al., "Rapamycin inhibits primary and metastatic tumor growth by antiangiogenesis: involvement of vascular endothelial growth factor," Nature Medicine, vol. 8, No. 2, Feb. 2002, pp. 128-135.
Gura, "Systems for Identifying New Drugs are Often Faulty," Science, vol. 278, Nov. 7, 1997, pp. 1041-1042.
Guvakova, M.A. et al., "Phosphorothioate oligodeoxynucleotides bind to basic fibroblast growth factor, inhibit its binding to cell surface receptors, and remove it from low affinity binding sites on extracellular matrix," The Journal of Biological Chemistry, vol. 278, No. 6, Feb. 10, 1995, pp. 2620-2627.
Hames, B.D. et al., "Nucleic Acid Hybridisation," Practical Approach Series, IRL Press, Oxford, 1985, 141 pages.
Han, J. et al., "Endothelial cell injury by high glucose and heparanase is prevented by insulin, heparin and basic fibroblast growth factor," Cardiovascular Diabetology, Aug. 9, 2005, vol. 4, Issue 12, pp. 1-12.
Hanahan, D. et al., "Patterns and emerging mechanisms of the angiogenic switch during tumorigenesis," Cell, vol. 85, Aug. 9, 1996, pp. 353-364.
Hasan, J. et al. "Intra-tumoural microvessel density in human solid tumours," British Journal of Cancer, vol. 86, 2002, pp. 1566-1577.
Hazlehurst, L.A. et al., "Adhesion to fibronectin via b1 integrins regulate p27 kip1 levels and contributes to cell adhesion mediated drug resistance (CAM-DR)," Oncogene, vol. 19, 2000, pp. 4319-4327.
Helmlinger, G. et al., "Interstitial pH and p02 gradients in solid tumors in vivo: high-resolution measurements reveal a lack of correlation," Nature Medicine, vol. 3, No. 2, Feb. 1997, pp. 177-182.
Hershkoviz, R. et al., "Differential effects of polysulfated polysaccharide on experimental encephalomyelitis, proliferation of auto-immune T cells, and inhibition of heparanase activity," Journal of Autoimmunity, vol. 8, No. 5, Oct. 1995, pp. 741-750. Abstract Only.
Imaginis.com, Centre for Women's Health, "Breast Health, Breast Cancer Glossary of Medical Terms" Retrieved from http://www.imaginis.com/glossary/breast-cancer-glossary-of-medical-terms-- 11, date unknown, 4 pages.
International Application No. PCT/IT2012/000193, International Preliminary Report on Patentability, dated Dec. 23, 2014, 8 pages.
International Application No. PCT/IT2012/000193, International Search Report and Written Opinion, dated Nov. 27, 2012, 12 pages.
International Preliminary Report on Patentability for International Application No. PCT/EP2015/077355, dated May 30, 2017, 7 pgs.
International Preliminary Report on Patentability for related International Application No. PCT/EP2004/009723, dated May 31, 2005, 7 pages.

(56) References Cited

OTHER PUBLICATIONS

International Preliminary Report on Patentability for related International Application No. PCT/EP2006/060304, dated Jun. 8, 2007, 7 pages.
International Preliminary Report on Patentability for related International Application No. PCT/EP2007/054633, dated Sep. 11, 2008, 7 pages.
International Preliminary Report on Patentability for related International Application No. PCT/EP2008/053461, dated Oct. 20, 2009, 11 pages.
International Preliminary Report on Patentability for related International Application No. PCT/EP2006/060306, dated Sep. 12, 2007, 6 pages.
International Preliminary Report on Patentability for related International Application No. PCT/IT2010/000451, dated May 14, 2013, 5 pages.
International Preliminary Report on Patentability for related International Application No. PCT/EP2009/053002 dated Sep. 21, 2010, 7 pages.
International Search Report and Written Opinion for International Application No. PCT/EP2015/077355, dated Jan. 22, 2016, 10 pgs.
International Search Report and Written Opinion for related International Application No. PCT/EP2004/009723, dated Dec. 22, 2004, 12 pages.
International Search Report and Written Opinion for related International Application No. PCT/EP2006/060304 dated Apr. 8, 2006, 8 pages.
International Search Report and Written Opinion for related International Application No. PCT/EP2006/060306 dated Sep. 25, 2006, 8 pages.
International Search Report and Written Opinion for related International Application No. PCT/EP2007/054633 dated Aug. 24, 2007, 9 pages.
International Search Report and Written Opinion for related International Application No. PCT/EP2008/053461 dated Oct. 9, 2008, 15 pages.
International Search Report and Written Opinion for related International Application No. PCT/EP2009/053002 dated Jun. 5, 2009, 11 pages.
International Search Report for International Application No. PCT/EP2002/013371, dated Jul. 23, 2003, 4 pgs.
International Search Report for International Application No. PCT/IT2010/000451, dated Jun. 22, 2011, 2 pgs.
Irony-Tur-Sinai, M. et al., "A synthetic heparin-mimicking polyanionic compound inhibits central nervous system inflammation," Journal of the Neurological Sciences, Jan. 2003, vol. 206, No. 1, Jan. 15, 2003, pp. 49-57. Abstract Only.
Isaji, M. et al, "Tranilast inhibits the proliferation, chemotaxis and tube formation of human microvascular endothelial cells in vitro and angiogenesis in vivo," British Journal of Pharmacology, vol. 122, 1997, pp. 1061-1066.
Japanese Patent Application No. 2013-538335, Official Notice of Rejection dated Sep. 24, 2014 (with English translation), 6 pages.
Jeffery, C.J. et al., "The *Escherichia coli* aspartate receptor: sequence specificity of a transmembrane helix studied by hydrophobic-biased random mutagenesis," Protein Engineering, vol. 12, No. 10, 1999, pp. 863-871.
Kainz, C. et al., "Prognostic value of tumour microvessel density in cancer of the uterine cervix stage IB to IIB," Anticancer Research, vol. 15, No. 4, Jul.-Aug. 1995; pp. 1549-1551.
Kaiser, "First Pass at Cancer Genome Reveals Complex Landscape," Science, vol. 313, Sep. 8, 2006, p. 1370.
Karlsson et al., "N-acetyl-L-cysteine promotes T-cell mediated immunity in allogeneic settings in vivo and in vitro," Oral Session 11: Immunotherapy/Experimental Graft-Versus-Host-Disease, 35th Annual Meeting of the European Group for Blood and Marrow Transplantation, Göteborg, Sweden, Mar. 31, 2009.
Kaushansky, K. et al, "Hematopoietic Growth Factors: Understanding Functional Diversity in Structural Terms," The Journal of the American Society of Hematology, Blood, vol. 82, No. 11, Dec. 1, 1993, pp. 3229-3240.
Kelland, "'Of mice and men': values and liabilities of the athymic nude mouse model in anticancer drug development," European Journal of Cancer, vol. 40, 2004, pp. 827-836.
Kerbel, "Human tumor Xenografts as Predictive Preclinical Models for Anticancer Drug Activity in Humans," Cancer Biology & Therapy, vol. 2, No. 4, Suppl. 1, Jul./Aug. 2003, pp. S134-S139.
Khaled, Z. et al., "Multiple mechanisms may contribute to the cellular anti-adhesive effects of phosphorothioate oligodeoxynucleotides," Nucleic Acids Research, vol. 24, No. 4, 1996, pp. 737-745.
Kochar, D.K. et al., "Sodium valproate for painful diabetic neuropathy: a randomized double-blind placebo-controlled study," QJM: An International Journal of Medicine, vol. 97, 2004, pp. 33-38.
Koehl, G.E. et al., "Defibrotide an endothelium protecting and stabilizing drug, has an anti-angiogenic potential in vitro and in vivo," Cancer Biology & Therapy, vol. 6, No. 5, May 2007, pp. 686-690.
Kojima, S. et al., "Enhancement of plasminogen activator activity in cultured endothelial cells by granulocyte colony-stimulating factor," Journal of Cellular Physiology, vol. 138, Jan. 1989, pp. 192-196. Abstract Only.
Kornblum, Noah, et al. "Defibrotide, a polydisperse mixture of single-stranded phosphodiester oligonucleotides with lifesaving activity in severe hepatic veno-occlusive disease: clinical outcomes and potential mechanisms of action." Oligonucleotides (2006); 16.1: 105-114.
Lee, S.J. et al., "Recognizing and Managing Chronic Graft-Versus-Host Disease," American Society of Hematology (2008) pp. 134-141.
Levidiotis, V. et al., "A synthetic heparanase inhibitor reduces proteinuria in passive heymann nephritis," Journal of the American Society of Nephrology, vol. 15, 2004, pp. 2882-2892.
Levidiotis, V. et al., "Heparanase inhibition reduces proteinuria in a model of accelerated anti-glomerular basement membrane antibody disease," Nephrology, vol. 10, 2005, pp. 167-173.
Levidiotis, V. et al., "Heparanase is involved in the pathogenesis of proteinnuria as a result of glomerulonephritis," Journal of the American Society of Nephrology, vol. 15, 2004, pp. 68-78.
Levidiotis, V. et al., "Increased expression of heparanase in puromycin aminonucleoside nephrosis," Kidney International, vol. 60, 2001, pp. 1287-1296.
Li, Q., et al., "Involvement of caspase-3 and p38MAPK in allogeneic CD8+T cell—induced apoptosis of vascular endothelial cells," Chinese Journal of Pathophysiology, 2009, vol. 25, Issue 9, Published Sep. 15, 2009, pp. 1671-1675 (English Abstract).
Maeshima, Y. et al., "Identification of the Anti-angiogenic Site within Vascular Basement Membrane-derived Tumstatin," The Journal of Biological Chemistry, vol. 276, No. 18, May 4, 2001, pp. 15240-15248.
Marni, A. et al. "Anti-ischemic effect of oligotide treatment in rat kidney: comparison with the effect of nifedipine and isosorbide dinitrate," Transplantation Proceedings, vol. 28, No. 1, Feb. 1996, pp. 301-303.
Marni, A. et al., "Protection of Kidney from Postischemic Reperfusion Injury in Rats Treated with Defibrotide," Transplantation Proceedings, vol. 22, No. 5, Oct. 1990, pp. 2226-2229.
Maxhimer, J.B. et al., "Heparanase-1 gene expression and regulation by high glucose in renal epithelial cells," Diabetes, Jul. 2005, vol. 54, pp. 2172-2178.
McDonald, G.B. et al., "Venocclusive Disease of the Liver after Bone Marrow Transplantation: Diagnosis, Incidence, and Predisposing Factors," Hepatology vol. 4, No. 1, 1984, pp. 116-122.
McDonald, G.B. et al., "Veno-occlusive Disease of the Liver and Multiorgan Failure after Bone Marrow Transplantation: A Cohort Study of 355 Patients," Annals of Internal Medicine, 1993;118:255-267.
Mitsiades, C.S. et al., "Defibrotide (DF) Targets Tumor-Microenvironmental Interactions and Sensitizes Multiple Myeloma

(56) References Cited

OTHER PUBLICATIONS and Solid Tumor Cells to Cytotoxic Chemotherapeutics," Blood (ASH Annual Meeting Abstracts), 2004, vol. 104, Abstract 286.
Mitsiades, C.S. et al., "Preclinical Studies in Support of Defibrotide for the Treatment of Multiple Myeloma and Other Neoplasias," Clin Cancer Res 2009;15(4), Feb. 15, 2009, pp. 1210-1221.
Mitsiades, C.S., "Defibrotide (DF) an Orally Bioavailable Modulator of Myeloma Tumor-Microenvironment Interactions: Molecular Sequetae and Clinical Implications," Blood (ASH Annual Meeting Abstracts), 2006 108: Abstract 3523, Poster Board #-Session: 752-III.
Mitsiades, C.S., et al., "Defibrotide (DF) has anti-neoplastic activity against multiple myeloma: Clinical implications for the incorporation of DF in cytotoxic chemotherapeutic regimes," Blood, vol. 102, No. 11, Nov. 16, 2003, p. 693a, Abstract 2567, Poster Board #-Session: 738-II.
Mondesire, W. et al., "Targeting Mammalian Target of Rapamycin Synergisticallly Enhances Chemotherapy-Induced Cytotoxicity in Breast Cancer Cells," Clinical Cancer Research, vol. 10, Oct. 2004, pp. 7031-7042.
Morabito, A. et al., "Antiangiogenic strategies, compounds, and early clinical results in breast cancer," Critical Reviews in Oncology/Hematology, vol. 49, 2004, pp. 91-107.
Murohara, T. et al., "Cardioprotective actions of oligotide, a single stranded polydeoxyribunucleotide complex, in myocardial ischaemia and reperfusion injury," British Journal of Pharmacology, vol. 117, 1996, pp. 1000-1008.
National Library of Medicine, "Defibrotide"—Medical Subject Heading, 2009 MeSH, MeSH Suplementary Concept Data.
Niada, R., et al., "PGI2-generation and antithrombotic activity of orally administered defibrotide," Pharmacological Research Communications, vol. 14, Issue 10, Nov. 1982, pp. 949-957. Abstract Only.
Nieuwenhuizen, W. et al., "Fluorogenic substrates for sensitive and differential estimation of urokinase and tissue plasminogen activator," Haemostasis, 7:146-149 (1978).
Orsino, A. et al., "Childhood acute myelomonocytic leukemia (AML-M4) presenting as catastrophic antiphospholipid antibody syndrome," Journal of Pediatric Hematology/Onocology, vol. 26, No. 5, May 2004, pp. 327-330.
Ostrovsky, O. et al., "Genetic variations in the heparanase gene (HPSE) associate with increased risk of GVHD following allogeneic stem cell transplantation: effect of discrepancy between recipients and donors." Blood, Mar. 18, 2010, vol. 115, No. 11, pp. 2319-2328.
Palmer, K.J., et al., "Defibrotide a Review of its Pharmacodynamic and Pharmacokinetic Properties, and Therapeutic Use in Vascular Disorders," Drugs, vol. 45, No. 2, 1993, pp. 259-294.
Parish, C.R. et al., "Heparanase: a key enzyme involved in cell invasion," Biochimica et Biophysica Acta, vol. 1471, 2001, M99-M108.
Parish, C.R. et al., "Treatment of central nervous system inflammation with inhibitors of basement membrane degradation," Immunology and Cell Biology, vol. 76, No. 1, Feb. 1998, pp. 104-113.
Pellegatta, F. et al., "The anti-ischemic drugs defibrotide and oligotide analogously inhibit leukocyte-endothelial cell adhesion in vitro," Transplant International, vol. 9, Suppl. 1, 1996, pp. S420-S424.
Persengiev, S.P et al., "Nonspecific, concentration-dependent stimulation and repression of mammalian gene expression by small interfering RNAs (siRNAs)," RNA, vol. 10, 2004, pp. 12-18.
Pescador, R. et al., "An Integrated View of the Activities of Defibrotide," Seminars in Thrombosis and Hemostasis, vol. 22, Suppl. 1, 1996, pp. 71-75.
Plaut, "p-Nitrobenzyl p-Toluenesulfonyl-L-Arginine: A Chromogenic Substrate for Thrombin, Plasmin, and Trypsin," Haemostasis, vol. 7: 105-108, 1978.
Podar, K. et al., "The pathophysiologic role of VEGF in hematologic malignancies: therapeutic implications," Blood, vol. 105, No. 4, Feb. 15, 2005, pp. 1383-1395.

Porta et al., "High-Performance Liquid Chromatography Determination of Polydeoxyribonucleotides in Plasma: Its Application to the Determination of Defibrotide's Pharmacokinetics in the Rabbit," Analytical Biochemistry, vol. 204: 143-146, 1992.
Prino, G. et al., Indagini preliminari sull'attivita fibrinolitica, nell'animale E nell'uomo, di una nuova sostanza presente in diversi organi animali, Simposio Internazionale, La Ricerca Scientifica Nell'Industria Farmaceutica in Italia, Risultati e Ruolo Internazionale, Roma, Oct. 2-4, 1975 (with English summary), 7 pages.
Prosper, F. et al., "Mobilization and Homing of Peripheral blood Progenitors Is Related to Reversible Downregulation of alpha4Beta1 Integrin Expression and Function," The American Society for Clinical Investigation, Inc., vol. 101, No. 11, Jun. 1998, pp. 2456-2467.
PureLink Brochure, "Nucleic Acid Purification" Invitrogen, 2007, 8 pages.
Ranieri et al., "Defibrotide in the treatment of Raynaud's phenomenon in patients with progressive systemic sclerosis or essential mixed cryoglobulinemia," Current Therapeutic Research, vol. 53:48-58,1993.
Richardson et al., "Defibrotide for the Treatment of Severe Hepatic Veno-Occlusive Disease and Multiorgan Failure after Stem Cell Transplanation: A Multicenter, Randomized, Dose-Finding Trial," Biol Blood Marrow Transplant 16: 1005-1017, 2010.
Richardson et al., "Multi-institutional use of defibrotide in 88 patients after stem cell transplantation with severe veno-occlusive disease and multisystem organ failure: response without significant toxicity in a high-risk population and factors predictive of outcome," Blood 100(13):4337-4343, 2002.
Richardson, P.G. et al., "Treatment of severe veno-occlusive disease with defibrotide: compassionate use results in response without significant toxicity in a high-risk population," Blood, vol. 92, No. 3, Aug. 1, 1998, pp. 737-744.
Rowlings, P.A. et al., "IBMTR Severity Index for grading acute graft-versus-host disease: retrospective comparison with Glucksberg grade," British Journal of Haematology, 1997, 97, pp. 855-864.
Ruutu, T et al., "Diagnostic criteria for hematopoietic stem cell transplant-associated microangiopathy: results of a consensus process by an International Working Group," haematologica/the hematology journal, 2007; 92(1):95-100.
Schroder, "Defibrotide protects endothelial cells, but not L929 tumour cells, from tumour necrosis factor-alpha-mediated cytotoxicity," Journal of Pharmacy and Pharmacology, vol. 47, 1995, pp. 250-252.
Simizu, S. et al., "Heparanase as a molecular target of cancer chemotherapy," Cancer Science, vol. 95, No. 7, Jul. 2004, pp. 553-558.
Stanford Health Care ECL sheet: 1 page total. Retrieved from the internet Oct. 7, 2016, 1 page.
Staton, C.A. et al., "Current methods for assaying angiogenesis in vitro and in vivo," International Journal of Experimental Pathology, vol. 85, 2004, pp. 233-248.
Stephan, S. et al., "Effect of Rapamycin Alone and in Combination with Antiangiogenesis Therapy in an Orthotopic Model of Human Pancreatic Cancer," American Association for Cancer Research.
Sun, H.C. et al., "Microvessel density of hepatocellular carcinoma: its relationship with prognosis," Journal of Cancer Research and Clinical Oncology, vol. 125, 1999, pp. 419-426.
Tai, BC et al., "Competing risks analysis of patients with osteosarcoma: a comparison of four different approaches," Statis. Med. 2001; 20:661-684.
Tamsma, J.T. et al., "Expression of glomerular extracellular matrix components in human diabetic nephropathy: decrease of heparan sulphate in the glomerular basement membrane," Diabetologia, vol. 37, 1994, pp. 313-320.
Trichon, B.H. et al., "Acute coronary syndromes and diabetes mellitus," Diabetes and Vascular Disease Research, vol. 1, Issue 1, May 2004, pp. 23-32.
Van Den Born, J. et al., "Distribution of GBM heparan sulfate proteoglycan core protein and side chains in human glomerular diseases," Kidney International, vol. 43, 1993, pp. 454-463.

(56) References Cited

OTHER PUBLICATIONS

Van't Veer, L.J. et al., "Gene expression profiling predicts clinical outcome of breast cancer," Nature, vol. 415, Jan. 31, 2002, pp. 530-536.
Verheul, H.M.W. et al., "Are tumours angiogenesis-dependent?," Journal of Pathology, vol. 202, 2004, pp. 5-13.
Vermuelen, M. et al., "Role of Adhesion Molecules in the Homing and Mobilization of Murine Hematopoietic Stem and Progenitor Cells," Blood, vol. 92, No. 3, Aug. 1, 1998, pp. 894-900.
Vingolo, E.M., et al., "Treatment of nonproliferative diabetic retinopathy with Defibrotide in noninsulin-dependent diabetes mellitus: A pilot study," Acta Opthalmologica, vol. 77, 1999, pp. 315-320.
Vlodavsky, I. et al., "Mammalian heparanse: Gene cloning, expression and function in tumor progression and metastasis," Nature Medicine, vol. 5, No. 7, Jul. 1999, pp. 793-802.
Vlodavsky, I. et al., "Molecular properties and involvement of heparanase in cancer metastasis and angiogenesis," The Journal of Clinical Investigation, vol. 108, No. 3, Aug. 2001, pp. 341-347.
Voskoglou-Nomikos, T. et al., "Clinical Predictive Value of the in Vitro Cell Line, Human Xenograft, and Mouse Allograft Preclinical Cancer Models," Clinical Cancer Research, vol. 9, Sep. 15, 2003, pp. 4227-4239.
Weidner, N. et al., "Tumor angiogenesis: a new significant and independent prognostic indicator in early-stage breast carcinoma," Journal of the National Cancer Institute, vol. 84, No. 24, Dec. 16, 1992, pp. 1875-1887.
Written Opinion for International Application No. PCT/IT2010/000451, dated Jun. 22, 2011, 4 pgs.
Xiangming, C. et al., "Angiogenesis as an unfavorable factor related to lymph node metastasis in early gastric cancer," Annals of Surgical Oncology, vol. 5, No. 7, 1998, pp. 585-589.
Yang, Y. et al., "Heparanase promotes the spontaneous metastasis of meloma cells to bone," Blood, vol. 105, No. 3, Feb. 1, 2005, pp. 1303-1309.

CELLULAR-BASED METHOD FOR DETERMINING THE BIOLOGICAL ACTIVITY OF DEFIBROTIDE

PRIORITY

This application is a 371 National Stage Entry of International Application PCT/EP2015/077355, filed Nov. 23, 2015, which claims priority to EP 14195277.0 filed Nov. 27, 2014, the contents of each of which are herein incorporated by reference in their entireties.

BACKGROUND OF THE INVENTION

Medicinal substances should be produced at a constant specific activity level so that they can be delivered safely. For example, assays for biological molecules such as heparin have variability from batch to batch in terms of chain length, molecular weight, composition, degree of sulphation, etc. Other substances that are extracted from natural substances also need to be standardized. See for example, U.S. Pat. No. 7,575,886. One such substance is defibrotide. Defibrotide is a heterogeneous mixture of single-stranded polynucleotides of varying lengths that is extracted from mammalian organs.

There are assays available to evaluate the biological activity of defibrotide, including the fibrin plate test and the thromboelastographic recording of the euglobulin lysis time (Prino G. et al., *Indagini preliminari sull'attivitfibrinolitica, nell'animale e nell'uomo, di una nuova sostanza presente in diversi organi animali*, Simposio Internazionale: La ricerca scientifica nell'industria farmaceutica in Italia, Rome, 2-4 Oct. 1975-11 Farmaco, Ed. Prat.) (1969),24,552-561), the plasmin method (U.S. Pat. No. 7,338,777), and the euglobulin method (WO2013/190582). Although these methods are useful pharmaceutical manufacturing tools, all these methods, which are based on the pro-fibrinolytic properties of defibrotide, involve an assessment of defibrotide's activity on isolated proteins or enzymes.

Thus, there is a need in the art for novel methods to determine the biological activity of defibrotide in a cellular context that provides an accurate and reliable process for assessing the potency, e.g., by comparison with a reference defibrotide standard preparation, of new batches of defibrotide regardless of the manufacturing process used.

SUMMARY OF THE INVENTION

The present invention is based, in part, on the discovery that defibrotide protects mammalian cells from cytotoxicity induced by particular cytotoxic agents in a dose-dependent manner. The inventors have taken advantage of this cell protection effect and developed a cell-based method for assessing the potency of defibrotide batches and defined a measurement unit to facilitate effective and safe administration. Such methods allow for, inter alia, quality control during the defibrotide manufacturing process, standardization of defibrotide batches produced by different methods or sources, and consistent dosing of patients with defibrotide.

DETAILED DESCRIPTION OF THE INVENTION

Figure 1:
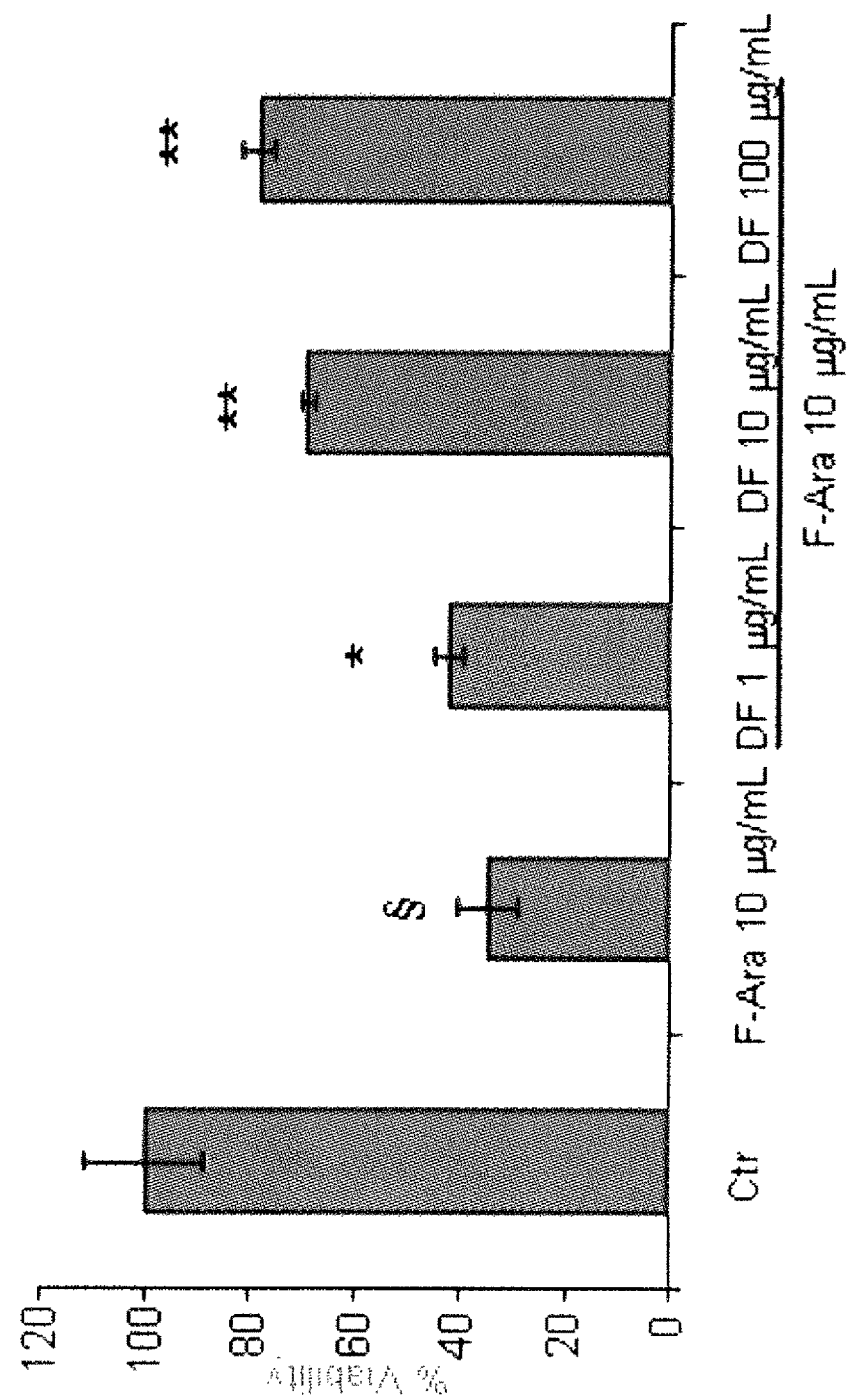
FIG. 1. Viability of HMEC cells incubated with fludarabine in the presence or absence of varying concentrations of defibrotide as measured by MTT assay. HMEC-1 were incubated with fludarabine (F-Ara) at 10 µg/ml in the presence or absence of varying concentrations of defibrotide (DF) (1 µg/ml-100 µg/ml) for 72 hr and the viability of the cells was measured with the MTT assay. Student t-test: §p<0.01, F-ara 10 µg/ml vs. control (ctr); * p<0.05, cells treated with DF at 1 µg/ml vs. F-ara 10 µg/ml; ** p<0.001, DF at 10 and 100 µg/ml vs. F-ara 10 µg/ml.

The present invention provides a reliable method for determining the biological activity of defibrotide based on the ability of defibrotide to protect living cells from the effects of certain cytotoxic agents. This cell protection effect is important for defibrotide's use as a medicinal product. This method allows for the standardization of the activity for defibrotide that is obtained by different methods or sources. The method also allows for the establishment and assignment of a unit of measurement to facilitate effective and safe administration of defibrotide. In one embodiment of the invention, the method of assessing the potency of a sample batch of defibrotide comprises (i) growing mammalian cells in culture, (ii) incubating the cells with a solution containing at least one cytotoxic agent and at least one concentration of defibrotide from the sample batch, (iii) determining the viability of the cells after an incubation period, and (iv) calculating the potency of the sample batch of defibrotide based on the cell viability measurement. In some embodiments, the method further comprises comparing the cell viability for the sample batch of defibrotide to the cell viability for a reference batch of defibrotide, and calculating the potency of the sample batch of defibrotide based on the comparison.

For the purpose of the present invention the term "potency" refers to the measure of the biological activity of defibrotide, in particular based on the measure of the ability of defibrotide to protect living cells from the effects of cytotoxic agents. Defibrotide (Merck Index, 1996, no. 2915; CAS number 83712-60-1) is a substance of natural origin. It is the sodium salt of low molecular weight polydeoxyribonucleotides which are obtained by extraction from animal organs. Defibrotide is known to have a molecular weight (MW) between 14 and 19 kDa, but specific measurement techniques show defibrotide to have an average molecular weight (MW) around 16.1 kDa±2.0 kDa if determined by SEC-HPLC technique; a MW around 17.6 kDa±1.0 kDa if determined by PAGE technique; and a MW around 16.7 kDa±1.6 kDa if determined by Multi-Angle Laser Light Scattering technique. "Analysis of Aggregates and Particles in Protein Pharmaceuticals" H. Mahler and W. Jiskoot (eds.), 2012 John Wiley & Sons, Inc. Defibrotide has numerous therapeutic applications, including use as an anti-thrombotic agent (U.S. Pat. No. 3,829,567), treatment of peripheral arteriopathies, treatment of acute renal insufficiency (U.S. Pat. No. 4,694,134), and treatment of acute myocardial ischaemia (U.S. Pat. No. 4,693,995). More recently, defibrotide has been used for the treatment and prevention of sinusoidal obstruction syndrome/venous occlusive disease (EU clinical trial EudraCT:2004-000592-33, US clinical trial 2005-01 (ClinicalTrials.gov identifier: NCT00358501). Other uses of defibrotide are described in the following patents and patent applications, each of which is hereby incorporated by reference in its entirety: U.S. Pat. Nos. 3,770,720; 3,829,567; 3,899,481; 4,693,134; 4,693,995; 4,938,873; 4,985,552; 5,081,109; 5,116,617; 5,223,609; 5,646,127; 5,646,268; 5,977,083; 6,046,172; 6,699,985; 6,767,554; 7,338,777; 8,551,967; 8,771,663, US Patent Publication Nos. 20080194506; 20090131362; 20110092576; 20130231470; 20140005256, U.S. patent application Ser. No. 14/323,918; and WO 2013/190582.

The methods described herein can be used to assess the potency of defibrotide batches manufactured by different methods or extracted from different animal organs. For instance, in some embodiments, the defibrotide sample batch is extracted from bovine tissue, such as bovine lung, intestine, or mucous membranes. In other embodiments, the defibrotide sample batch is extracted from porcine tissue, such as porcine lung, intestine, or mucous membranes. Defibrotide sample batches may also be extracted from other organs from other animal species, including sheep and horses.

In certain embodiments, the defibrotide sample batches to be evaluated for potency by the methods described herein are manufactured by a process such as that described in U.S. Pat. Nos. 4,985,552 and 5,223,609, both of which are hereby incorporated by reference in their entireties. In particular, the defibrotide obtained with this process is a polydeoxyribonucleotide corresponding to the following formula of random sequence:

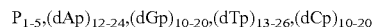

wherein:
P=phosphoric radical
dAp=deoxyadenylic monomer
dGp=deoxyguanylic monomer
dTp=deoxythymidylic monomer
dCp=deoxycytidylic monomer.

The defibrotide sample batches may have one or more or all of the following chemico-physical properties: electrophoresis=homogeneous anodic mobility; extinction coefficient, $E_{1cm}^{1\%}$ at 260±1 nm=220±10; extinction ratio, $E_{230}/E_{260}$=0.45±0.04; coefficient of molar extinction (referred to phosphorus), $\varepsilon(P)$=7750±500; rotary power $[\alpha]D^{20°}$=53°±6; reversible hyperchromicity, indicated as % in native DNA, h=15±5; and a purine:pyrimidine ratio of 0.95±0.5. In certain embodiments, the defibrotide sample batches to be evaluated for potency by the methods of the invention may have been subjected to a physiochemical stress or suspected of being exposed to a physiochemical stress, such as high temperature, extreme pH, hydrogen peroxide, etc. Thus, the methods of the invention can also be used to assess the potency of defibrotide batches or compositions comprising defibrotide that have been stored at sub-optimum conditions or for extended periods of time. In certain embodiments, the methods can be used to monitor the stability of defibrotide batches or compositions comprising defibrotide, for example, to predict shelf-life.

The methods of the invention comprise growing mammalian cells in culture. In certain embodiments, the mammalian cells are human cells. In some embodiments, the human cells are human epithelial cells. In other embodiments, the human cells are human endothelial cells. In one particular embodiment, the human endothelial cells are human liver sinusoidal endothelial cells, such as SK-HEP-1 cells. In another particular embodiment, the human endothelial cells are human microvascular endothelial cells, such as HMEC-1 cells. In another particular embodiment, the epithelial cells are keratinocytes (e.g. HaCaT cells) or alveolar epithelial cells (e.g. A549 cells). Mammalian cells can be obtained from recognized depositories, such as the American Type Culture Collection (ATCC) as well as other sources.

Suitable growth media for growing mammalian cells in culture are well known in the art and are disclosed for instance in "Culture of Animal Cells: A Manual of Basic Technique and Specialized Applications" R. I. Freshney, 2010, Wiley-Blackwell. The optimal medium for each type of cells can be obtained from specialised suppliers of the cells (e.g.: ATCC-LGC, MI, Italy; CDC, Atlanta, Ga., USA). In certain embodiments, the mammalian cells are grown in Eagle's Minimum Essential Medium (EMEM) supplemented with 10% (v/v) fetal bovine serum (FBS), 100 units/mL Penicillin, 100 µg/mL Streptomycin, and 2.5 µg/mL Amphotericin B. In other embodiments, the mammalian cells are grown in RPMI 1640 medium supplemented with 10% (v/v) fetal bovine serum (FBS), 100 units/mL Penicillin, 100 µg/mL Streptomycin, and 2.5 µg/mL Amphotericin B. In certain embodiments, the growth media may contain L-glutamine (e.g. 2 mM), hydrocortisone (e.g. 10 µg/ml), and epidermal growth factor (e.g. 10 µg/ml). The density of the mammalian cells may be from about $5 \times 10^4$ cells/ml to about $5 \times 10^5$ cells/ml, from about $2.5 \times 10^4$ cells/ml to about $2.5 \times 10^5$ cells/ml, or from about $5 \times 10^4$ cells/ml to about $2 \times 10^5$ cells/ml. In order to obtain optimal assay response, the cell density may, in certain embodiments, be optimised taking into account the nature of the cytotoxic agent and the type of cell used for the assay. For example, in embodiments in which human endothelial cells are used for the assay, particularly suitable cell densities range from about $2.5 \times 10^4$ cells/ml to about $2 \times 10^5$ cells/ml, preferably about $5 \times 10^4$ cells/ml. These cell densities are particularly suitable for assays in which doxorubicin or fludarabine is the cytotoxic agent.

In another aspect of the invention, the methods comprise incubating the mammalian cells in culture with a solution comprising a cytotoxic agent and at least one concentration of defibrotide from the sample batch under evaluation. As used herein, the term "cytotoxic agent" refers to a compound that has a toxic effect on a cell, such as inducing cell necrosis, inhibiting cell growth or cell division, or inducing cell apoptosis. The cytotoxicity of compounds can result from various properties, including, but not limited to, anti-metabolite properties, alkylating properties, nucleic acid intercalating properties, or apoptotic properties.

An anti-metabolite property is the ability of the compound, or its metabolites, to interfere with the proper synthesis of biomolecules, such as DNA and RNA.

Examples of compounds having an anti-metabolite property include nucleobase analogs (e.g. purine and pyrmidine analogs), nucleoside and nucleotide analogs, and antifolate compounds. Exemplary nucleobase and nucleoside analogs that have cytotoxic effects include, but are not limited to, azathioprine, thiopurines (e.g. thioguanine, mercaptopurine), fludarabine, pentostatin, 5-fluorouracil, 6-azauracil, clofarabine, nelarabine, cladribine, cytarabine, floxuridine, capecitabine, gemcitabine, azacitidine, and decitabine. Examples of antifolates include methotrexate, aminopterin, pemetrexed, pralatrexate, and raltitrexed.

An alkylating property is the ability of the compound, or its metabolites, to transfer alkyl groups to biomolecules or form covalent bonds with reactive groups within biomolecules (e.g. amino, carboxyl, sulfhydryl, and phosphate groups), which can inactivate or interfere with their biological function. Many alkylating agents can cross-link DNA strands impairing DNA replication, which can lead to the induction of apoptosis. Examples of alkylating agents include nitrogen mustards (e.g. mechlorethamine, cyclophosphamide, melphalan, chlorambucil, ifosfamide and busulfan), nitrosoureas (e.g. N-Nitroso-N-methylurea, carmustine, lomustine, and semustine, fotemustine and streptozotocin), tetrazines (e.g. dacarbazine, mitozolomide and temozolomide), aziridines (e.g. thiotepa, mytomycin and diaziquone), and cisplatins (e.g. cisplatin, carboplatin and oxaliplatin).

A nucleic acid intercalating property is the ability of the compound, or its metabolites, to insert into the DNA double helix, which can cause mutations, or intercalate within regions of helical structures of RNA. Examples of intercalating agents include ethidium bromide, mitomycin, actinomycin, plicamycin, anthracyclines (e.g. doxorubicin, daunorubicin, epirubicin, idarubicin, valrubicin, and mitoxantrone), thalidomide and bleomicins.

An apoptotic property is the ability of the compound, or its metabolites, to induce programmed cell death. One particular class of compounds that can induce apoptosis is anti-microtubule agents, which interfere with mitosis and result in cell cycle arrest, thereby inducing apoptosis. Anti-microtubule agents include vinca alkaloids, such as vincristine, vinblastine, vinorelbine, vindesine, and vinflunine, and taxanes, such as paclitaxel and docetaxel.

Topoisomerase inhibitors also are cytotoxic by virtue of their ability to prevent DNA replication and transcription and/or by causing DNA strand breaks, thereby inducing apoptosis. Topoisomerase inhibitors include, but are not limited to, irinotecan, topotecan, etoposide, doxorubicin, mitoxantrone and teniposide.

The cytotoxic agent used in the methods of the invention is generally a synthetic, semi-synthetic, or natural chemical compound. The compound may have one or more of the properties described above. The cytotoxic agent can be any of the compounds described herein or a metabolite thereof. In some embodiments, the cytotoxic agent may be selected from fludarabine, cytarabine, 5-fluorouracil, methotrexate, busulfan, melphalan, cisplatin, ethidium bromide, doxorubicin, anthracyclines, thalidomide, or combinations thereof. In certain embodiments, the cytotoxic agent used in the methods of the invention is fludarabine or its active metabolite, 9-beta-D-arabinofuranosyl-2-fluoroadenine (F-Ara-A). In other embodiments, the cytotoxic agent used in the methods of the invention is doxorubicin.

Alternative cytotoxic agents commonly known to the person skilled in the art are equally suitable for use in the methods of the present invention. For example, in some embodiments, the cytotoxic agents slow or arrest cell cycle progression, and/or induce apoptosis of cells. Such types of cytotoxic agents include Staurosporine, Bendamustine, Carmustine, Imatinib and salts thereof (marketed as Gleevec), Ara-C, Gemtuzumab (such as Gemtuzumab ozogamicin, marketed as Mylotarg), Azacitidine (marketed as Vidaza), Decitabine (marketed as Dacogen), Vorinostat (marketed as Zolinza), and Thapsigargin, H202, and Phorbol Myristate Acetate. See also the NIOSH list of Antineoplastic and Other Hazardous Drugs in Healthcare Settings 2012, HHS, Publication No. 2012-150.

The concentration of the cytotoxic agent used in the methods of the invention will vary depending on the particular cytotoxic agent and mammalian cell type being used. In embodiments in which fludarabine or F-Ara-A is the cytotoxic agent, the agent is present in the growth medium at a final concentration from about 10 µg/ml to about 50 µg/ml. In other embodiments in which doxorubicin is the cytotoxic agent, the agent is present in the growth medium at a final concentration from about 0.1 µg/ml to about 10 µg/ml.

The cytotoxic agents may be used singly or in combination of 2, 3, 4, 5, 6, or more agents. In certain embodiments, the potency of a single sample batch of defibrotide may be assessed by evaluating independently its cell protection effect for two different cytotoxic agents. By way of example, a first potency value of the defibrotide sample batch may be obtained by performing the method with a first cytotoxic agent (e.g. fludarabine) and a second potency value may be obtained by performing the method with a second cytotoxic agent (e.g. doxorubicin). An overall potency of the defibrotide sample batch may be determined by a mathematical comparison of the first and second potency values, for example by averaging the two value or calculating a ratio of the two values.

In certain embodiments, a particular set of culture conditions may be used to induce cytotoxicity of the mammalian cells rather than employing a specific cytotoxic agent or agents. For instance, the methods may comprise exposing mammalian cells to an apoptosis-inducing culture medium in the presence of at least one concentration of defibrotide, determining the viability of the cells after an incubation period, and calculating the potency of the defibrotide based on the cell viability measurement. An apoptosis-inducing culture medium can include medium having an acidic pH (e.g. pH of about 2 to about 6 or about 4.5 to about 6.5) or a basic pH (e.g. pH of about 7.5 to about 10 or about 8 to about 9.5). Apoptosis-inducing culture medium also includes medium that does not contain essential growth factors (e.g. fibroblast growth factor, epidermal growth factor, platelet-derived growth factor) as withdrawal of growth factors is recognized as an inducer of apoptosis. As used herein, "apoptosis-inducing medium" can also refer to medium at a particular temperature range (e.g. greater than 37° C.) or oxygen concentration range (less than 5% oxygen) that induces apoptosis. The apoptosis-inducing culture medium or conditions can be readily adjusted by a person of ordinary skill in the art for the particular mammalian cell type being employed in the methods. U.V. or other types of radiation can also be used to induce apoptosis. In some embodiments, the incubation solution comprises at least one concentration of defibrotide from the sample batch under evaluation in addition to the cytotoxic agent. The concentration of defibrotide from the sample batch (e.g. final concentration in cell-containing medium) can be in the range from about 1 µg/ml to about 1 mg/ml, from about 1 µg/ml to about 100 µg/ml, from about 1.25 µg/ml to about 80 µg/ml, or from about 5 µg/ml to about 50 µg/ml.

In certain embodiments, multiple concentrations of the defibrotide from the sample batch are tested. For instance, in one embodiment, at least two different concentrations of defibrotide from the sample batch are separately tested. In another embodiment, at least three different concentrations of defibrotide from the sample batch are separately tested. In a particular embodiment, at least four different concentrations of defibrotide from the sample batch are separately tested. The multiple concentrations of defibrotide from the sample batch are preferably within the ranges disclosed above. In some embodiments, the multiple concentrations of the defibrotide from the sample batch are prepared by successive 1:2 dilutions of a stock solution.

In some embodiments, the method further comprises testing a reference defibrotide batch simultaneously with the defibrotide sample batch. The reference defibrotide batch is typically tested at various known concentrations of defibrotide. Multiple concentrations of the reference defibrotide batch may, in some embodiments, be tested. As with the multiple concentrations of the defibrotide sample batch, the multiple concentrations of the defibrotide reference batch can be prepared by serial dilution of a stock solution in accordance with a predetermined dilution factor. The concentrations of the defibrotide from the reference batch are preferably in the same concentration range as the concentrations from the defibrotide from the sample batch. For example, the concentrations of defibrotide from the reference batch (e.g. final concentration in cell-containing medium) can be from about 1 µg/ml to about 1 mg/ml, from about 1 µg/ml to about 100 µg/ml, from about 1.25 µg/ml to about 80 µg/ml, or from about 5 µg/ml to about 50 µg/ml.

In some embodiments of the method, at least 4 concentrations of the defibrotide sample batch and the defibrotide reference batch are prepared with at least 3 replicates for each concentration of the sample batch and reference batch.

In certain embodiments, the methods comprise a positive control of cytotoxicity. For instance, the mammalian cells are incubated with the cytotoxic agent alone (i.e. without any defibrotide) under the same conditions.

In some embodiments, the methods comprise a negative control of cytotoxicity. For example, in one embodiment, the mammalian cells are incubated in a solution without any defibrotide or cytotoxic agent under the same conditions. Such solutions may contain the cell growth medium and optionally any vehicle or solvent.

In one particular embodiment, the incubation of the mammalian cells with the cytotoxic agent with and without defibrotide (reference and sample batches, positive and negative controls) is conducted in a multi-well microtiter plate (e.g. 96-well). The subsequent determination of cell viability may also be performed in the microtiter plate. In some related embodiments, the wells of the microtiter plate are coated with a cell attachment matrix, such as poly-D-lysine.

The incubation period to obtain an acceptable assay response can be optimised, in relation to the cytotoxic agent and type of cell used in the method. One of skill in the art can adjust these parameters based on the common general knowledge.

In certain embodiments of the methods, the cells may be incubated with the cytotoxic agent and defibrotide from the sample and/or reference batches for a period ranging from about 12 to about 120 hours, from about 24 to about 96 hours, from about 48 to about 72 hours, or from about 48 to about 96 hours. In one embodiment, the incubation period is at least about 24 hours. In another embodiment, the incubation period is at least about 48 hours. In still another embodiment, the incubation period is at least about 72 hours.

Suitable incubation conditions for specific mammalian cell types can be found in general laboratory manuals, such as "Culture of Animal Cells: A Manual of Basic Technique and Specialized Applications" R. I. Freshney, 2010, Wiley-Blackwell. The set points for temperature and % $CO_2$ during the incubation period are other variables that can be adjusted to optimize the assay response. According to one embodiment of the present invention, the mammalian cells are incubated at a temperature ranging from between about 35° C. to about 39° C. In another embodiment, the mammalian cells are incubated at a temperature ranging from between about 36° C. and about 38° C. According to a further aspect of the present invention, the mammalian cells are incubated at a $CO_2$ concentration ranging from about 0 to about 10% (v/v) to maintain an optimal pH of the medium for cell growth. In another embodiment, the $CO_2$ concentration may be from about 1 to about 5%.

In another aspect of the methods of the invention, the viability of the mammalian cells is determined following incubation with the cytotoxic agent and defibrotide from a sample batch. Multiple techniques are available to assess cellular viability (see, e.g., Assay Guidance Manual, NCBI, 2013, G. Sitta Sittampalam et al. Eds.; Stoddart MJ., Cell viability assays: introduction; Methods Mol Biol. 2011;740: 1-6 and Riss et al., ASSAY and Drug Development Technologies, Vol. 2(1): 51-62, 2004, both of which are hereby incorporated by reference in their entireties), and any specific techniques described herein are illustrative only. In some embodiments, cell viability is assessed by using commercially available kits, such as the Cell Counting Kit 8 (Dojindo Molecular Technology Inc.; Sigma-Aldrich) and those available from Life Technologies and Thermo Scientific.

Some suitable methods for determining cell viability that can be used with the methods of the invention include methods of assessing membrane integrity, assays measuring reduction or oxidation, methods that measure cellular ATP content, mitochondrial activity assays, and caspase assays. Methods of assessing membrane integrity (e.g. cytolysis or membrane leakage assays) include vital dye exclusion methods, such as those utilizing trypan blue, propidium iodide, erythrosin B or 7-Aminoactinomycin D, lactose dehydrogenase assays, and assays for protease biomarkers. Such methods generally entail measuring the presence of intracellular enzymes in the extracellular milieu (e.g. lactose dehydrogenase) or the presence of membrane impermeable dyes intracellularly as indications of compromised cell membranes.

Redox-based assays are typically colorimetric or fluorimetric methods in which certain classes of compounds (dyes/stains) change color or fluorescence as a result of biochemical reactions carried out by living cells. One example of these types of assays include the MTT assay in which cellular oxidoreductase enzymes reduce the tetrazolium dye MTT 3-(4,5-dimethylthiazol-2-yl)-2,5-diphenyltetrazolium bromide to its insoluble formazan, which has a purple color. Other closely related tetrazolium dyes can be used in similar assays to measure cellular viability. Thus, in certain embodiments of the methods of the invention, cell viability is determined by performing a colorimetric assay based on the reduction of tetrazolium dyes. Suitable tetrazolium dyes include 3-(4,5-dimethylthiazol-2-yl)-2,5-diphenyltetrazolium bromide (MTT), 2,3-bis-(2-methoxy-4-nitro-5-sulfophenyl)-2H-tetrazolium-5-carboxanilide (XTT), 3-(4,5-dimethylthiazol-2-yl)-5-(3-carboxymethoxyphenyl)-2-(4-sulfophenyl)-2H-tetrazolium (MTS), and water soluble tetrazolium salts, such as WST-1 and WST-8 (2-(2-methoxy-4-nitrophenyl)-3-(4-nitrophenyl)-5-(2,4-disulfophenyl)-2H-tetrazolium). Such techniques are well known in the art and are described, for instance, in Mosmann, "Rapid colorimetric assay for cellular growth and survival: application to proliferation and cytotoxicity assays," J Immunol Methods. 1983 Dec. 16; 65: 55-63, which is hereby incorporated by reference in its entirety. A similar redox-based assay for determining cell viability utilizes the fluorescent dye, resazurin (7-Hydroxy-3H-phenoxazin-3-one 10-oxide). Resazurin is reduced to highly red fluorescent resorufin in live cells and thus cell viability can be determined by measuring the increase in fluorescence in the presence of the dye.

Cell viability can also be assessed by measuring changes in intracellular processes, such as changes in intracellular free radicals (e.g. reactive oxygen species, nitric oxide), free ion concentration (e.g. $Ca^{2+}$, $Mg^{2+}$, $Zn^{2+}$), and membrane potential. Fluorescence indicators to monitor and quantitate such changes are commercially available from various sources, such as the fluorescent-based reagents available from Life Technologies and Promega. One such assay involves the use of calcein AM, which is a cell permeable dye that is a substrate for cellular esterases. Enzymatic activity in live cells converts calcein AM to a fluorescent product thereby allowing the determination of the number of live cells by increases in fluorescence. Quantitation of adenosine triphosphate (ATP) content has also been used as a marker of cell viability. Cellular ATP content can be measured by the amount of light produced through reaction with the luciferase enzyme using, for example, a luminometer.

In some embodiments, cell viability may be measured manually, for example by counting living cells with the aid of suitable microscopes or by means of suitable equipment evaluating the absorbance/fluorescence change, selected from a spectrophotometer, a spectrofluorimeter, a flow cytometer or a combination thereof. Other techniques for assessing cell viability are known to those of skill in the art and may be adopted for use with the methods of the present invention. Depending on the assay used to assess cell viability, the cell viability measurement may be a change in the absorbance or fluorescence of the cell-containing solution or medium, a percentage or number of living cells, or a percentage or number of dead cells. In some embodiments, a change in absorbance or fluorescence can be converted into a percentage or number of living cells or dead cells. For instance, in embodiments in which a change in color or fluorescence occurs as a result of a dye or stain permeating a compromised cell membrane (e.g. trypan blue, erythrosin B or propidium iodide), an increase in absorbance or fluorescence at a particular wavelength indicates an increase in the number of dead cells. In other embodiments in which a change in color or fluorescence occurs as a result of a cellular reaction (e.g. MTT assay, calcein AM assay), the number of live cells correlates with an increase in absorbance or fluorescence at a particular wavelength. Thus, in certain embodiments of the methods of the invention, cell viability is determined by measuring the absorbance or fluorescence of the solution containing the mammalian cells following incubation with the cytotoxic agent and defibrotide. In one embodiment, the cell viability (e.g. absorbance or fluorescence) for each concentration of defibrotide from the sample batch (e.g. absorbance/fluorescence of each well of the microtiter plate containing different concentrations of defibrotide from the sample batch) is measured and plotted against the corresponding concentration of defibrotide to create a dose-response curve. In some embodiments, the dose-response curve is a sigmoidal curve (i.e. "S-shaped"). The range of defibrotide concentrations that are tested may be expanded or additional number of concentrations added to obtain a sigmoidal dose-response curve.

The absorbance or fluorescence readings or other cell viability measurements (e.g. number or percentage of live cells; e.g. number or percentage of dead cells) for each of the samples (e.g. the positive and negative controls, defibrotide reference batch and defibrotide sample batch), known as raw data, can be processed and subject to further statistical analysis. Dedicated software can be employed for statistical analysis, such as that especially designed for bioassay evaluation like, for example, PLA 2 (Stegmann Systems GmbH, Germany) or, alternatively, a commercial off-the shelf spreadsheet customised for the statistical evaluation of biological assay data.

In certain embodiments, the methods of the invention comprise comparing the cell viability measured for samples containing the sample batch of defibrotide to the cell viability measured for a reference batch of defibrotide. In some embodiments, the cell viability measurements for the reference batch of defibrotide were obtained prior to the analysis of the sample batch of defibrotide. Such prior measurements for reference batches of defibrotide can be stored in a reference database or computer readable storage medium. In certain embodiments the cell viability measurements for the reference batch represent an average of cell viability measurements obtained from a population of defibrotide reference batches. Thus, potency of the defibrotide sample batch can be calculated based on the cell viability measurements for the sample batch by comparison to a standard calibration curve obtained from prior analysis of a defibrotide reference batch or population of defibrotide batches. In other embodiments, the cell viability measurements for the reference batch of defibrotide are acquired at the same time as the cell viability measurements for the sample batch of defibrotide. For example, a series of concentrations for the defibrotide sample batch are run in parallel with a series of concentrations for the defibrotide reference batch.

The reference batch of defibrotide is preferably a standardized defibrotide batch having a known biological activity (e.g. pro-fibrinolytic activity, cell protection activity). For instance, in one particular embodiment, the reference batch of defibrotide has a cell protection activity of between 630-905 Units/mg. The standardized defibrotide batch can have one or more of the following characteristics: an average molecular weight of between about 14 to about 19 kDa as measured by SEC-HPLC, an extinction coefficient ($\epsilon 1\%$) of about 207-233, an extinction ratio (Emin/Emax) of about 0.41-0.49, a purine to pyrimidine ratio greater than about 0.80 (e.g. about 0.80 to about 1.50), coefficient of molar extinction ($\epsilon(P)$, referred to phosphorus) of about 7200 to about 8400, rotary power ($[\alpha]D^{20°}$) of about 45° to about 60°, and reversible hyperchromicity, indicated as % in native DNA (h) of about 8 to about 22. In some embodiments, the reference batch of defibrotide is a batch of defibrotide manufactured under GMP conditions for clinical use. In other embodiments, the reference batch of defibrotide is a commercial batch of defibrotide available from Gentium (Villa Guardia, Italy).

In some embodiments, cell viability measurements for multiple concentrations of defibrotide from the reference batch are acquired to create a calibration curve. In one embodiment, creation of the calibration curve comprises the acquisition of the absorbance data relating to the samples at known increasing concentrations of defibrotide from the reference batch and the statistical processing of those data to obtain the calibration curve, which represents the correlation between the increase in cell viability in the presence of a cytotoxic agent and the dose of defibrotide. In certain embodiments, the cell viability measured for the sample batch of defibrotide is compared to a calibration curve obtained from cell viability measurements with a reference batch of defibrotide to determine the potency of the sample batch of defibrotide.

In some embodiments, a dose-response curve obtained from cell viability measurements from the defibrotide sample batch is compared to the calibration curve obtained from cell viability measurements with a reference batch of defibrotide. In such embodiments, the dose-response curve and the calibration curve may be sigmoidal curves (see FIG. 7, for example). The difference between the two curves is a function of the difference in biological activity between the defibrotide sample batch and the defibrotide reference batch. This difference is the potency of the sample batch of defibrotide compared to the reference batch. In one embodiment, a four-parameter logistic function model (4-PL, European Pharmacopoeia, section 5.3.2) is used to determine the difference between the dose-response curve for the defibrotide sample batch and the calibration curve for the defibrotide reference batch to calculate the potency of the sample batch of defibrotide. In another embodiment, a five-parameter logistic function model (5-PL, R. A. Dudley et al., "Guidelines for immunoassay data processing," Clin. Chem., 1985, 31: 1264-1271) is used to determine the difference between the dose-response curve for the defibrotide sample batch and the calibration curve for the defibrotide reference batch to calculate the potency of the sample batch of defibrotide.

In some embodiments, the data obtained from the cell viability measurements of samples with the defibrotide sample batch can be evaluated for additional statistical parameters to ensure the data are valid. For example, the data can be required to satisfy certain statistical criteria, such as those mandated by regulatory agencies. Such tests may include tests for linearity, parallelism, and linear regression at the significance level of, for example 0.05, such that, $F_{non-linearity} < F_{critical}$, $F_{non-parallelism} < F_{critical}$, and $F_{Regression} > F_{critical}$, respectively as detailed in for example, European Pharmacopoeia, section 5.3.2, 2014 and United States Pharmacopeia Chapter (1034) Analysis of Biological Assays, 2014.

The potency of the defibrotide sample batch calculated from statistical methods above can be expressed as a percent of the defibrotide reference batch, protection activity units per weight of defibrotide, or other units that may or may not be arbitrary. In some embodiments, a defibrotide protection unit is the concentration of defibrotide that mediates half-maximal cell-protection of SK-HEP-1 cells in the presence of 10 µg/ml fludarabine under the given assay conditions. In one embodiment, the potency of the defibrotide sample batch is expressed as a potency ratio relative to the potency of the reference batch of defibrotide. In certain embodiments, the potency ratio for the defibrotide sample batch is calculated using the following formula:

$$\text{Potency Ratio} = C_{ref}/C_{samp}$$

Where, C is the concentrations of reference (ref) and sample (samp) defibrotide materials required to achieve the same effect.

The methods of assessing potency of a defibrotide sample batch as described herein can be used in the preparation of pharmaceutical compositions comprising defibrotide to adjust the quantity of defibrotide included in the compositions to ensure the compositions comprise accurate and consistent dosages. Thus, the methods of the invention can be used during the manufacturing process to assess the potency of different batches of defibrotide prepared at different locations, by different methods, or from different sources.

The methods of the invention can also be used to monitor the stability of defibrotide batches or pharmaceutical compositions comprising defibrotide over time. For instance, the potency of a batch or composition can be determined by the methods described herein periodically over time (e.g., monthly, biannually, annually) or following exposure to extreme conditions to monitor the activity of the defibrotide and identify batches or compositions that have deteriorated or degraded.

These and other aspects of the invention will be better illustrated in the following examples, which are not, however, to be regarded as limiting the invention.

All patent and non-patent documents referenced throughout this disclosure are incorporated by reference herein in their entirety for all purposes.

EXAMPLES

Materials and Methods

The following materials were used in the Examples given here below.

Apparatus

A Victor 3 microplate reader equipped with different emission and absorption filters (Perkin Elmer, Milan, Italy), operated by Wallac software (Perkin Elmer, Milan, Italy).

Single and multi-channel pipettes with continuous volume adjustment equipped with sterile tips for molecular biology (Gilson, Milan, Italy.

Cell incubator with temperature and $CO_2$ control (Thermo Fischer Scientific, Milan, Italy.

Laminar flow hoods for tissue culture model HERAcell-150 (Thermo Fischer Scientific, Milan, Italy).

Analytical balance AX 26 DR (Mettler, Milan, Italy).

pH meter model 780 (Metrohom Italia, Milan, Italy).

Cell culture flasks, 25 and 75 $cm^2$, vent cap (Corning Incorporated, NY, USA).

Sterile, clear 96 well poly-D-lysine coated or uncoated (Sigma Aldrich, Milan, Italy).

Neubauer counting chamber and optical microscope (Carl Zeiss, Milan, Italy).

Vacuum medium filter sterilization unit (Sigma Aldrich, Milan, Italy?).

Computer Programs

Microsoft Excel 2003. (Microsoft Corporation, Redmond, Wash., USA)

PLA 2 (Stegmann Systems GmbH, Germany)

Cells

Human Microvascular Endothelial Cell line (HMEC-1, CDC, Atlanta, Ga., USA)

Liver sinusoidal endothelial cell line (SK-HEP-1, ATCC, Manassas, Va., USA)

Reagents and Chemicals

Defibrotide (Gentium, Italy)

9-beta-D-arabinofuranosyl-2-fluoroadenine, analytical grade (Sigma Aldrich, Milan, Italy), referred to as fludarabine or F-ara in the Figures and Examples below Doxorubicin, analytical grade (Sigma Aldrich, Milan, Italy)

Amphotericin B (Sigma-Aldrich, Milan, Italy)

Dimethyl sulfoxide (DMSO) (Sigma-Aldrich, Milan, Italy)

Gelatin, 2% in water, tissue culture grade (Sigma-Aldrich, Milan, Italy)

Dulbecco's phosphate buffered saline (D-PBS) (Sigma-Aldrich, Milan, Italy)

Ethanol Absolute (Sigma-Aldrich, Milan, Italy)

Fetal Bovine Serum (FBS) (Sigma-Aldrich, Milan, Italy)

Penicillin-Streptomycin 100X (Sigma-Aldrich, Milan, Italy)

MTT (Sigma-Aldrich, Milan, Italy)

CCK-8 (Sigma Aldrich, Milan, Italy)

Trypan Blue (Sigma-Aldrich, Milan, Italy)

Eagle's Minimum Essential Medium (EMEM) ATCC Number: 30-2003 (ATCC Manassas, Va., USA)

Oligonucleotide $(ACGT)_n$ of about 17 Kda (Sigma Genosys, Milan, Italy)

Oligonucleotide (AC), of about 17 KDa (Sigma Genosys, Milan, Italy)

Glutathione (Sigma-Aldrich, Milan, Italy)

Human tissue plasminogen activator (tPA) (Sigma-Aldrich, Milan, Italy)

Molecular biology grade water (Sigma-Aldrich, Milan, Italy)

Preparation of Cell Growth Medium for SK-HEP-1

Cell growth medium for SK-HEP-1 was Eagle's Minimum Essential Medium (EMEM) supplemented with 10% (v/v) of foetal bovine serum (FBS), 1× Penicillin-Streptomycin and 1× Amphotericin B. From 500 ml of EMEM medium 65 ml was removed and 50 ml of FBS, 5 ml of a 100× concentrate of Penicillin-Streptomycin stock and 10 ml 50× concentrate of Amphotericin B stock was added. The medium was filter sterilised using a medium filter sterilisation unit.

Preparation of Cell Growth Medium for HMEC-1

Cell growth medium for HMEC-1 was RPMI 1640 medium supplemented with 10% (v/v) FBS, 1× Penicillin-Streptomycin and 1× Amphotericin B. From 500 ml of RPMI 1640 medium 65 ml was removed and 50 ml of FBS, 5 ml of a 100× concentrate of Penicillin-Streptomycin stock and 10 ml 50× concentrate of Amphotericin B stock, 2 mM L-glutamine, 10 µg/ml hydrocortisone was added. The medium was filter sterilised using a medium filter sterilisation unit and sterile epidermal growth factor was added to a concentration of 10 µg/ml.

SK-HEP-1 Cultivation and Preparation

The human liver sinusoidal endothelial cell line SK-HEP-1 was obtained from the American Type Culture Collection (ATCC) and cultured in complete EMEM medium in a humidified cell incubator containing 5% $CO_2$ at 37° C. using gelatin-coated tissue culture flasks. The cells were sub-cultured by trypsin mediated detachment every 2-3 days following the instructions provided by the ATCC. Cells were serially transferred into culture flasks when the culture was 80-90% confluent and used for the protection assay between passages +3 to +10. That is, 3 to 10 passages beyond the characterised passage number of the cells received from the ATCC.

A suspension of SK-HEP-1 for use in the cell protection assay was prepared and counted. Briefly the cells were washed with D-PBS, and detached using 1 ml of trypsin solution and resuspended in complete medium to a cell concentration of $10^5$, $2×10^5$ or $4×10^5$ cells/ml. Cells were counted using a Neubauer counting chamber in the presence of trypan blue to assess the percent viability of the cultures. The cell culture used in the cell protection assay had a viability of ≥90%.

HMEC-1 Cultivation and Preparation

The human microvascular endothelial cell line (HMEC-1) was obtained from the Centers for Disease Control and Prevention (CDC) and cultured in complete RPMI 1640 medium in a humidified cell incubator containing 5% $CO_2$ at 37° C. The cells were sub-cultured by trypsin mediated detachment every 2-3 days and serially transferred into culture flasks when the culture was 80-90% confluence and used for the protection assay between passages +3 to +10.

A suspension of HMEC-1 for use in the cell protection assay was prepared and counted. Briefly the cells were washed with D-PBS, and detached using 1 ml of trypsin solution and resuspended in complete medium to a cell concentration of $10^5$, $2×10^5$ or $4×10^5$ cells/ml. Cells were counted using a Neubauer counting chamber in the presence of trypan blue to assess the percent viability of the cultures. The cell culture used in the cell protection assay had a viability of ≥90%.

Preparation of Stock Solutions

1. Fludarabine

A 10 mg vial of Fludarabine was dissolved in 1 ml of DMSO to give a solution of 10 mg/ml and stored at 4° C. The stock solution was diluted 1:1 with complete growth medium to give the working stock solution of 5 mg/ml.

2. Defibrotide

Defibrotide stock solution was prepared on the day of use. Approximately 100 mg of defibrotide drug substance was accurately weighed into a 50 ml sterile tube and dissolved in 20 ml of D-PBS to give a solution of 5 mg/ml. This solution was diluted 1:10 with complete growth medium to give the working stock solution of 0.5 mg/ml used to produce the concentration dilution series.

3. Tissue Plasminogen Activator (tPA)

The content of two 10 μg vials of t-PA (about 400,000 IU/mg per vial) were dissolved in 2 ml of D-PBS to give a solution of 4000 IU/ml and stored at −80° C.

4. ACGT Oligonucleotide,

A 1 mg vial of ACGT oligonucleotide was dissolved in 2 ml of D-PBS to give a solution of 0.5 mg/ml and stored at 4° C.

5. Glutathione 100 mg of glutathione were dissolved in 20 ml of PBS? and diluted 1:10 with complete growth medium to a final concentration of 0.5 mg/ml.

6. Doxorubicin

A 10 mg vial of doxorubicin was dissolved in 10 ml DMSO and stored at −80° C. A working stock was prepared by dilution in complete medium to 200 μg/ml.

Plate Depositions

Fifty μl of the cell suspensions, or medium alone for blanks, prepared at the concentrations described above was placed in wells of a poly-D-lysine coated 96-well microtiter plate. The plates were placed in the cell incubator for 3 hr after which 50 μl of the challenge solution was added to cell-containing wells. Three or four replicate wells were used for each experimental condition. For example, the preparation of solutions containing fludarabine in the absence or presence of defibrotide is given in Table 1. Following addition of the solution to the wells, the plates were returned to the incubator and cell viability was assessed after 24, 48 or 72 hr. For a background measurement, 100 μl of complete medium alone was included in 3 to 4 replicate wells.

TABLE 1

Preparation of fludarabine and defibrotide solutions

| Sample type | Defibrotide (*) (μg/ml) | Medium (μl) | Fludarabine Stock (μl) | Defibrotide Stock (μl) |
| --- | --- | --- | --- | --- |
| Negative Control | 0 | 3486 | 14 | 0 |
| Defibrotide Sample 1: 1 | 1.25 | 3468.5 | 14 | 17.5 |
| Defibrotide Sample 1: 2 | 2.5 | 3451 | 14 | 35 |
| Defibrotide Sample 1: 4 | 5 | 3416 | 14 | 70 |
| Defibrotide Sample 1: 8 | 10 | 3346 | 14 | 140 |
| Defibrotide Sample 1: 16 | 20 | 3206 | 14 | 280 |
| Defibrotide Sample 1: 32 | 40 | 2926 | 14 | 560 |
| Defibrotide Sample 1: 64 | 80 | 2366 | 14 | 1120 |
| Blank | 0 | 3500 | 0 | 0 |

(*) final concentration in each well following addition of 50 μL of cell suspension and 50 μL of the indicated solution Cell Viability Using MTT Assay After the specified period of incubation, cell viability in each well was measured using the MTT assay. The MTT assay is based on the cleavage of tetrazolium salts by mitochondrial dehydrogenase in viable cells leading to the production of an insoluble formazan dye. MTT dye, 10 μl of a 2 mg/ml solution in D-PBS, was added to each well and then the plates were incubated for 3 hours. Plates were then centrifuged and each well aspirated. The dye was solubilised with 200 μl of a mixture DMSO/Ethanol (1:1) and absorbance in the wells was read at 570-590 nm on a microplate reader. A blank well containing only media and cytotoxic drug (fludarabine or doxorubicin) was also run as a control in all experiments.

Cell Viability Using CCK-8 Assay

After the specified period of incubation, cell viability in each well was measured using the CCK-8 cell counting kit (Sigma Aldrich, Milan, Italy) following the manufacturer's instructions. The assay is based on the reduction by dehydrogenase activities of viable cells of the water soluble tetrazolium salt WST-8 (2-(2-methoxy-4-nitrophenyl)-3-(4-nitrophenyl)-5-(2,4-disulfophenyl)-2H-tetrazolium). The reduced formazan dye is soluble in tissue culture media. The amount of the formazan is directly proportional to the number of viable cells. The detection sensitivity of CCK-8 is higher than the other tetrazolium salts such as MTT. Unlike MTT, no solubilisation step is required and thus the assay can be measured continuously.

Briefly, after the specified incubation time, 10 μl of the supplied reagent was added to each well of the microtitre plate and the plate returned to the incubator. After 3 hours, the absorbance was measured at 450 nm with a background correction at 590 nm. Absorbance of the medium blank was subtracted from the test samples.

Example 1

The present example shows the magnitude of the protection effect of defibrotide against fludarabine-induced cytotoxicity of HMEC-1 cells at physiologically relevant concentrations of fludarabine and defibrotide.

HMEC-1 cells were cultivated according to the above mentioned procedure. A cell density of 500,000 cells/ml was used for the assay. The cytotoxic agent was fludarabine at a concentration of 10 μg/ml. Defibrotide was added to the microplate well at a concentration of 100, 10 or 1 μg/ml. Four replicates of each condition were performed. The viability of the HMEC cells was assessed after 72 hours with the MTT assay described above. Defibrotide protected the cells from fludarabine-induced cytotoxicity in a dose-dependent manner with a protection effect of more than 50% observed with 100 μg/ml of defibrotide (FIG. 1).

Example 2

The present example shows the magnitude of the protection effect of defibrotide against doxorubicin-induced cytotoxicity of SK-HEP-1 cells at physiologically relevant concentrations of doxorubicin and defibrotide.

Figure 2:
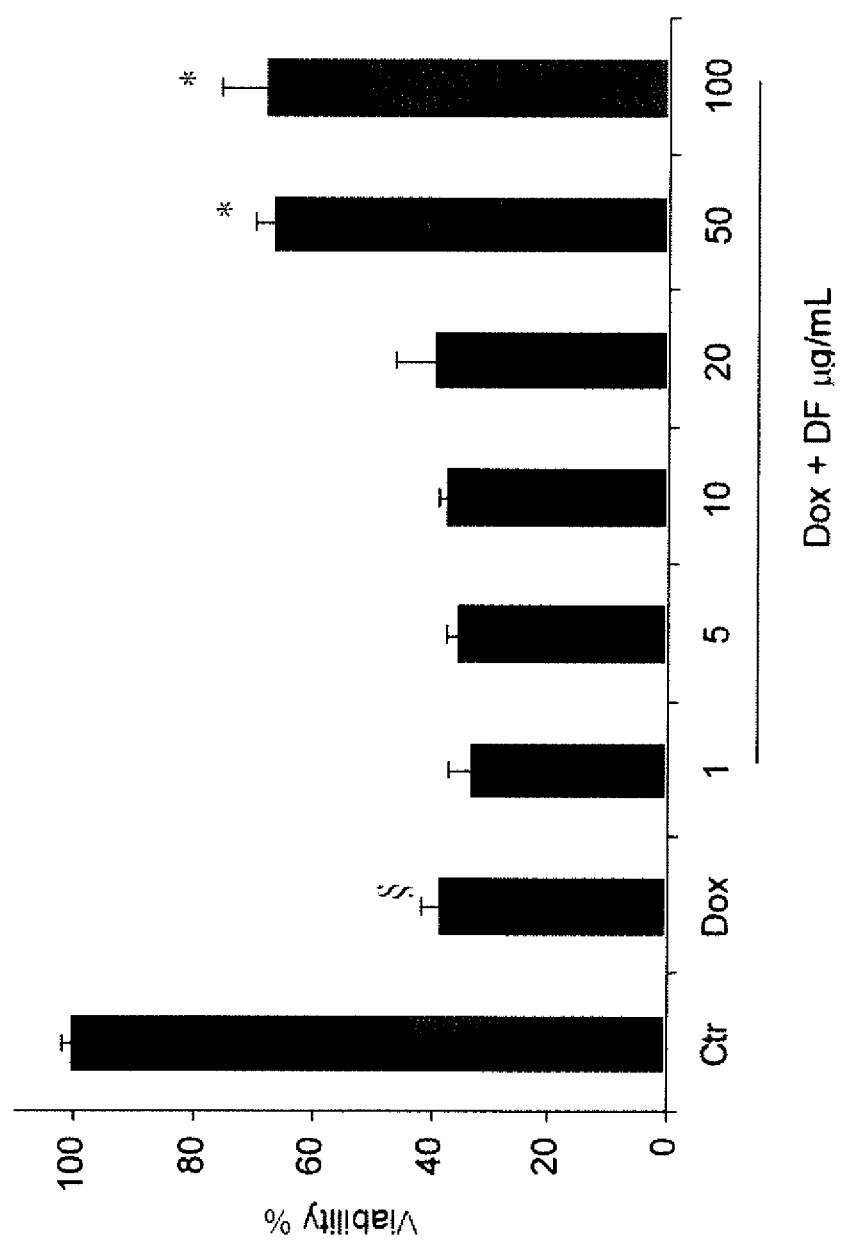
FIG. 2. Viability of SK-HEP-1 cells incubated with doxorubicin in the presence or absence of varying concentrations of defibrotide as measured by CCK-8 assay. SK-HEP-1 cells were incubated with doxorubicin (Dox) at 0.1 µg/ml in the presence or absence of varying concentrations of defibrotide (DF) (1 µg/ml-100 µg/ml) for 72 hr and the viability of the cells was measured with the CCK-8 assay. Student t-test: §p<0.01, Dox 0.1 µg/ml vs. control (ctr); * p<0.01, cells treated with DF at 50 or 100 µg/ml vs. Dox 0.1 µg/ml.

SK-HEP-1 cells were grown according to the above mentioned procedure. A cell density of about 50,000 cells/ml was used for the experiment. The cytotoxic agent was doxorubicin at a concentration of 0.1 µg/ml. Defibrotide was added to the microplate well at a concentration of 100, 50, 20, 10, 5 or 1 µg/ml. Three replicates of each condition were performed. The viability was assessed after 72 hours with the CCK-8 assay kit as described above. At concentrations of 50 µg/ml or greater, defibrotide significantly protected SK-HEP-1 cells from doxorubicin-induced cytotoxicity. (FIG. 2).

Example 3

The present example compares the protective effective against fludarabine-induced cytotoxicity of defibrotide and synthetic oligonucleotides having similar average length and base composition to defibrotide.

HMEC-1 cells were cultivated according to the above mentioned procedure. A cell density of about 500,000 cells/ml was used for the experiment. The cytotoxic agent was fludarabine at a concentration of 50 µg/ml. Synthetic oligonucleotides (Adenine-Cytosine (AC) of about 16 kDa or Adenine-Cytosine-Guanine-Thymine (ACGT) of about 17 kDa) or defibrotide were added to each well at varying concentrations. Specifically, the AC oligonucleotides were added to each well at a concentration of 1, 10, 100 or 500, whereas the ACGT oligonucleotides were added to each well at a concentration of 12.5, 25 or 50 µg/ml. Defibrotide was added to each well at a concentration of 5, 25, 50, or 100 µg/ml. Each treatment condition was performed in triplicate. The viability was assessed with the MTT assay after 24, 48 and 72 hours.

Figure 3A:
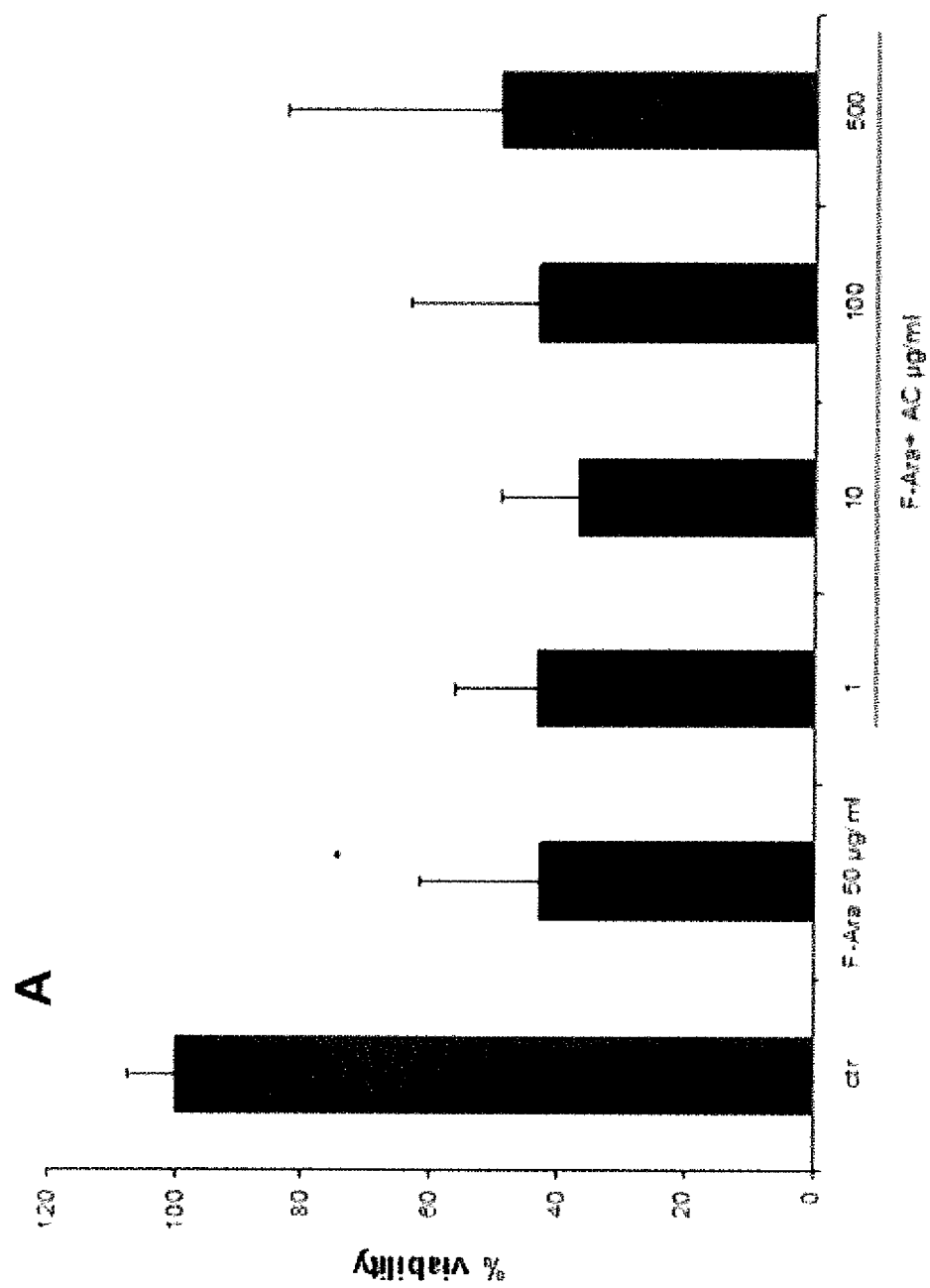
FIG. 3. Viability of HMEC-1 cells incubated with fludarabine in the presence or absence of varying concentrations of defibrotide, AC or ACTG as measured by MTT assay. HMEC-1 cells were incubated with fludarabine (F-Ara) at 50 µg/ml in the presence or absence of varying concentrations of random synthetic Adenine-Cytosine (AC) oligonucleotides of about 16 kDa (1-500 µg/ml) (FIG. 3A), random synthetic Adenine-Cytosine-Guanine-Thymine (ACGT) oligonucleotides of about 17 kDa (12.5-50 mg/ml) (FIG. 3B), or defibrotide (5-100 µg/ml) (FIG. 3C) for 72 hr and the viability of the cells was measured with the MTT assay. Student t-test: * p<0.01, F-ara 50 µg/ml vs. control (Ctr), ** p<0.01 F-ara 50 µg/ml vs. defibrotide. There was no significant protection by either of the synthetic oligonucleotides.
Figure 3B:
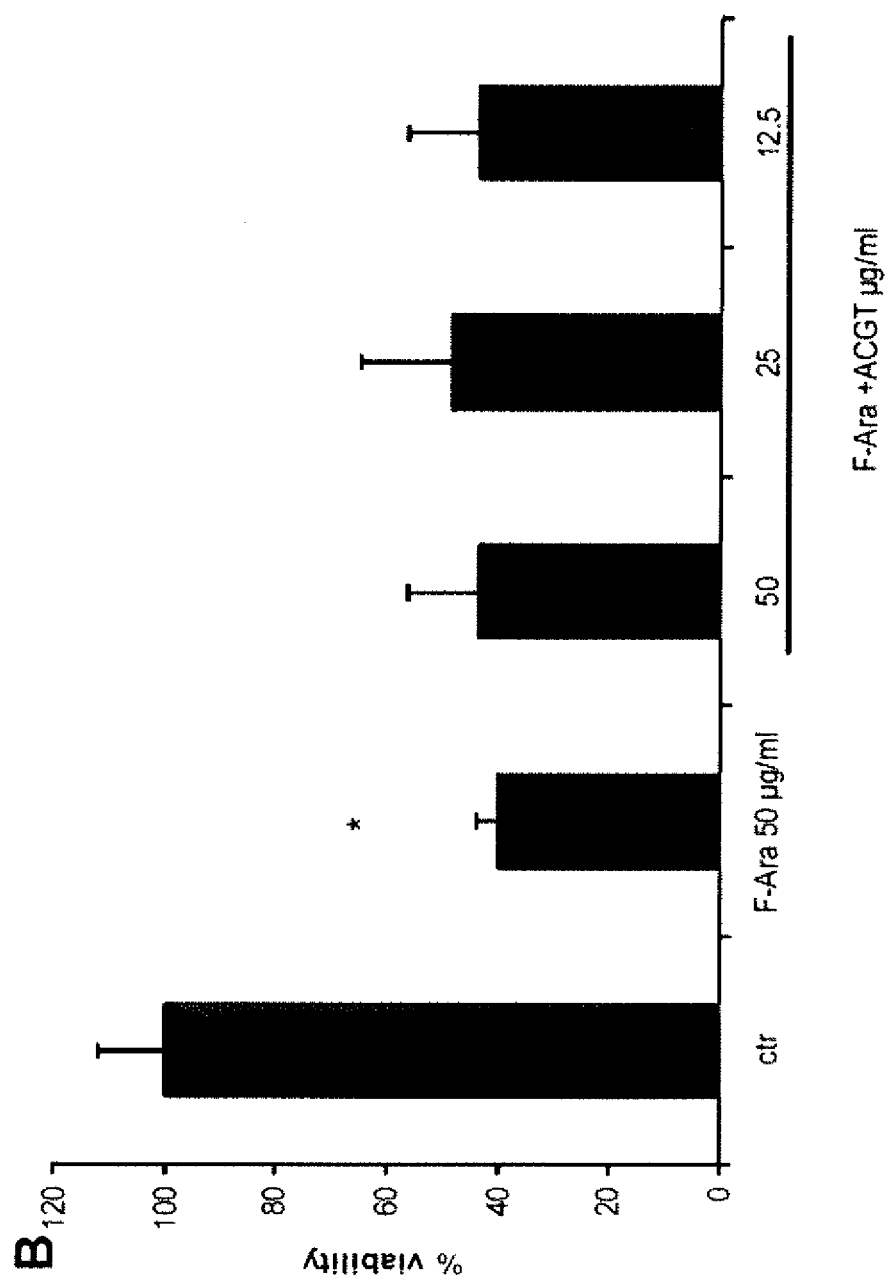
Figure 3C:
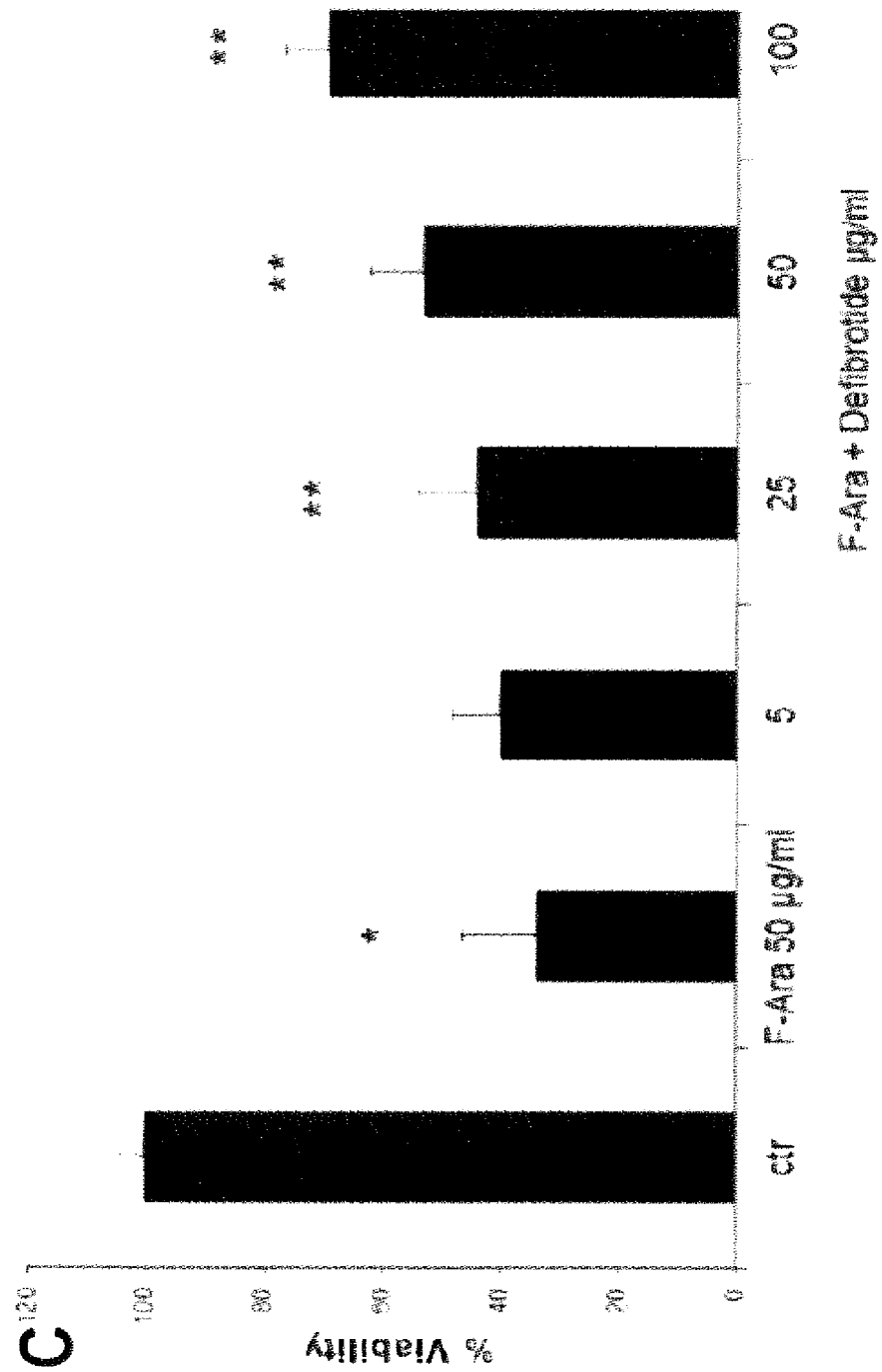

As shown in FIGS. 3A and 3B, neither the AC oligonucleotides nor the ACGT oligonucleotides had any protective effect against fludarabine-induced cytotoxicity of HMEC-1 cells after 72 hours of incubation. In contrast, defibrotide exhibited a dose-dependent protection of the cells from fludarabine-induced cytotoxicity (FIG. 3C).

Example 4

The experiments described in this example tested the ability of a synthetic ACGT oligonucleotide, tPA, and glutathione to protect SK-HEP-1 cells from fludarabine-induced toxicity.

SK-HEP-1 cells were grown and expanded according to the above mentioned procedure. A cell density of about 50,000 cells/ml was used for the experiment. The cytotoxic agent was fludarabine at a concentration of 10 µg/ml. A random synthetic oligonucleotide (ACGT), tPA, or glutathione was added to each well at varying concentrations. Specifically, the ACGT oligonucleotide or glutathione was added to each well at a concentration of 1.25, 2.5, 5, 10, 20, 40, or 80 µg/ml, whereas tPA was added at a concentration of 10, 20, 40, 80, 160, or 320 IU/ml.

Figure 4:
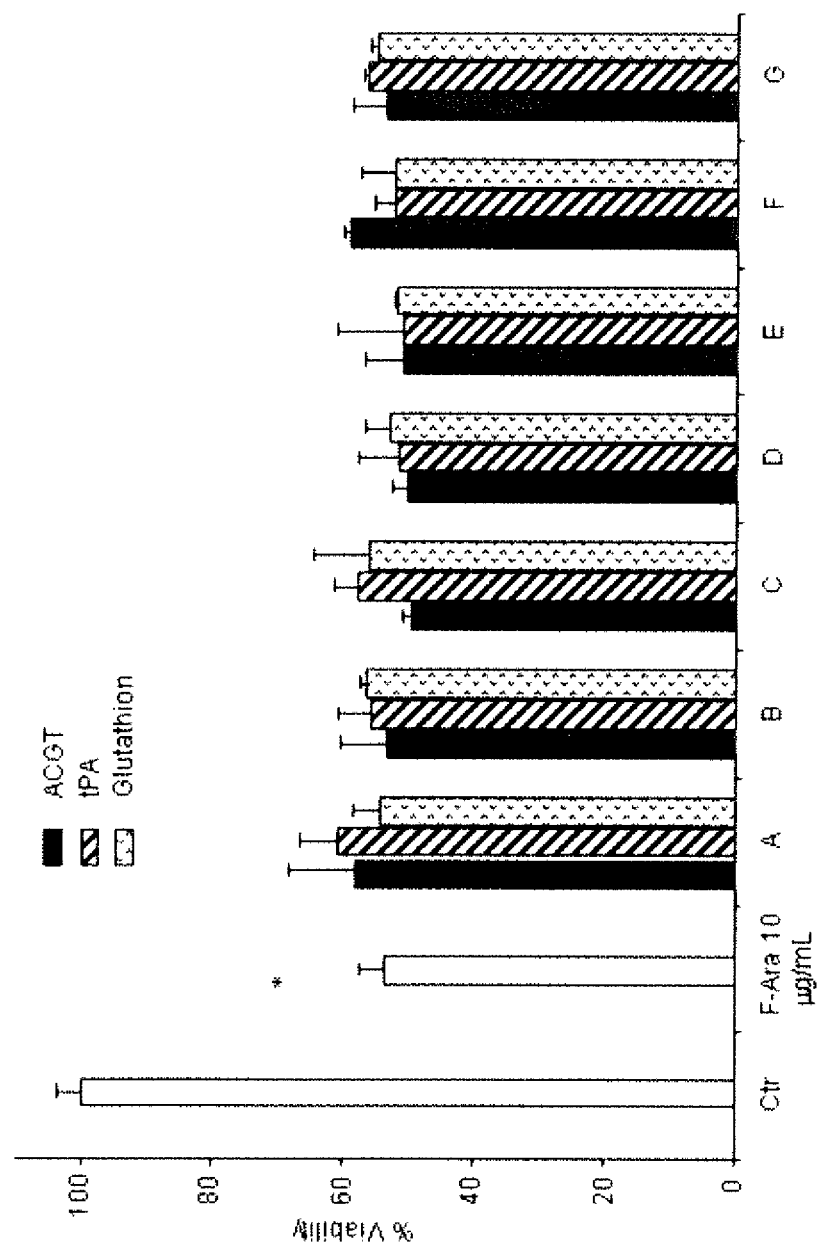
FIG. 4. Viability of SK-HEP-1 cells incubated with fludarabine in the presence or absence of varying concentrations of ACTG, tpA, or glutathione as measured by CCK-8 assay. SK-HEP-1 cells were incubated with fludarabine (F-Ara) at 10 µg/ml in the absence or presence, (A-G), of varying concentrations of random synthetic Adenine-Cytosine-Guanine-Thymine (ACGT) oligonucleotides of about 17 kDa (1.25-80 µg/ml), tPA (10-320 IU/ml), or glutathione (1.25-80 µg/ml) for 72 hr and the viability of the cells was measured with the CCK-8 assay. Student t-test: * p<0.01, F-Ara 10 µg/ml vs. control (Ctr). There was no significant protection from F-Ara-induced cytotoxicity by ACGT, tPA, or glutathione.

Each treatment condition was performed in triplicate. The viability was assessed with the CCK-8 assay kit after 72 hours incubation. No protection of the SK-HEP-1 cells from fludarabine-induced cytotoxicity was observed with any of the three compounds (FIG. 4).

Example 5

The present example evaluates the protective effective against fludarabine-induced cytotoxicity of defibrotide which has been modified as a result of physicochemical stress.

Defibrotide samples were stressed by submitting a standard sample of defibrotide to either 1) an Acidic Stress or 2) a Basic Stress. The Acidic Stress entailed incubating the standard defibrotide sample in a phosphate buffer having a pH of about 3 at about 80° C. for 18 hours. The Basic stress involved incubating the standard defibrotide sample in a phosphate buffer having a pH of about 12 at about 80° C. for 18 hours. After the incubation period, the solutions were brought to neutrality with phosphoric acid or sodium hydroxide.

SK-HEP-1 cells were grown according to the above mentioned procedure. A cell density of about 50,000 cells/ml was used for the experiment. The cytotoxic agent was fludarabine at a concentration of 10 µg/ml. Standard defibrotide (unmodified), defibrotide submitted to acid stress, or defibrotide submitted to basic stress were added to each well at a concentration of 80, 40, 20, 10, 5, 2.5, or 1.25 µg/ml. Each treatment condition was performed in triplicate.

Figure 5A:
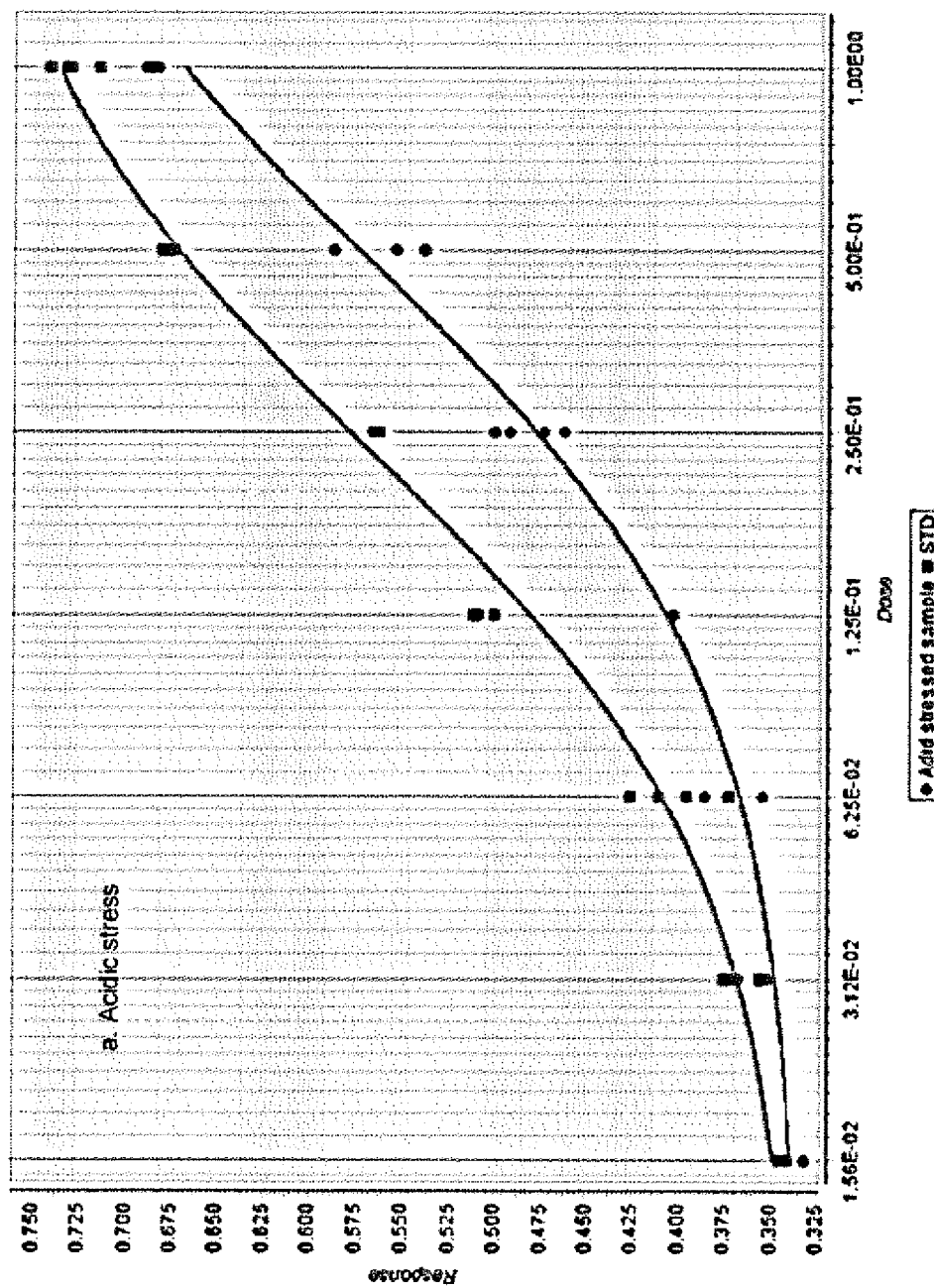
FIG. 5. Comparison of the dose response curves of standard defibrotide versus acid-stressed (FIG. 5A) and basic-stressed (FIG. 5B) defibrotide samples in the cell protection assay. The raw absorbance data was processed using the PLA2 statistical analysis program (4-parameter logistic function analysis). Absorbance of the cell viability indicator dye (CCK-8) is plotted on the Y-axis as "response." Dose is plotted on the X-axis and is a 2-fold dilution series of defibrotide in the assay (1.25-80 µg/ml); STD represents the reference standard defibrotide. The lower traces in each panel, which correspond to the stressed samples, indicate a reduced potency. Using this statistical analysis program, both stressed samples failed to meet the statistical criteria of acceptance.
Figure 5B:
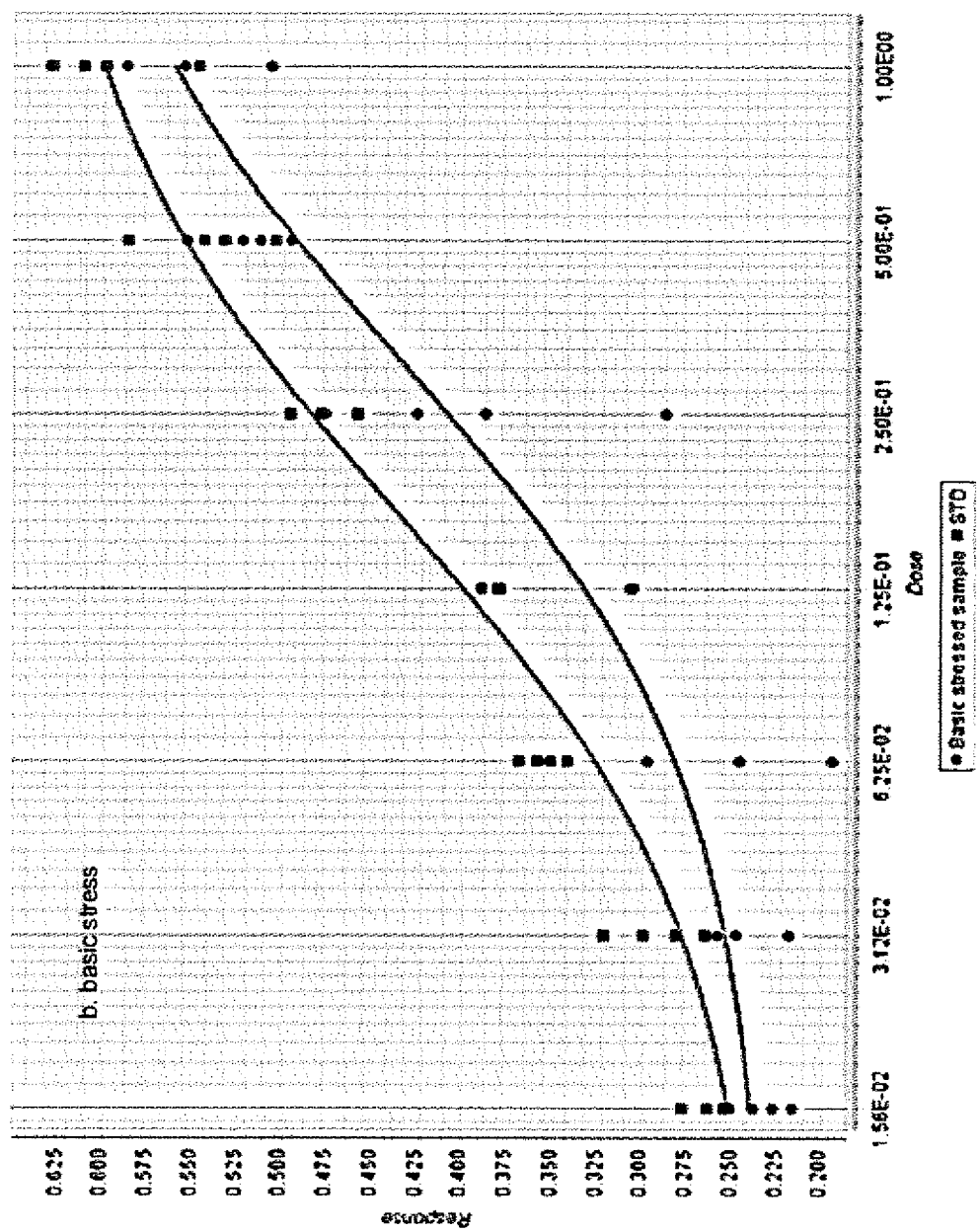

The viability of the cells was assessed with the CCK-8 assay kit after 72 hours incubation. Dose-response curves were constructed for unmodified defibrotide, acid-stressed defibrotide, and basic-stressed defibrotide. A comparison of the dose-response curves is shown in FIG. 5. Both the acid-stressed and basic-stressed defibrotide samples were less potent than unmodified defibrotide in protecting SK-HEP-1 cells from fludarabine-induced cytotoxicity (FIG. 5).

Example 6

The present example shows the magnitude of the protection effect of defibrotide against fludarabine-induced cytotoxicity of SK-HEP-1 cells at physiologically relevant concentrations of defibrotide and fludarabine.

Figure 6:
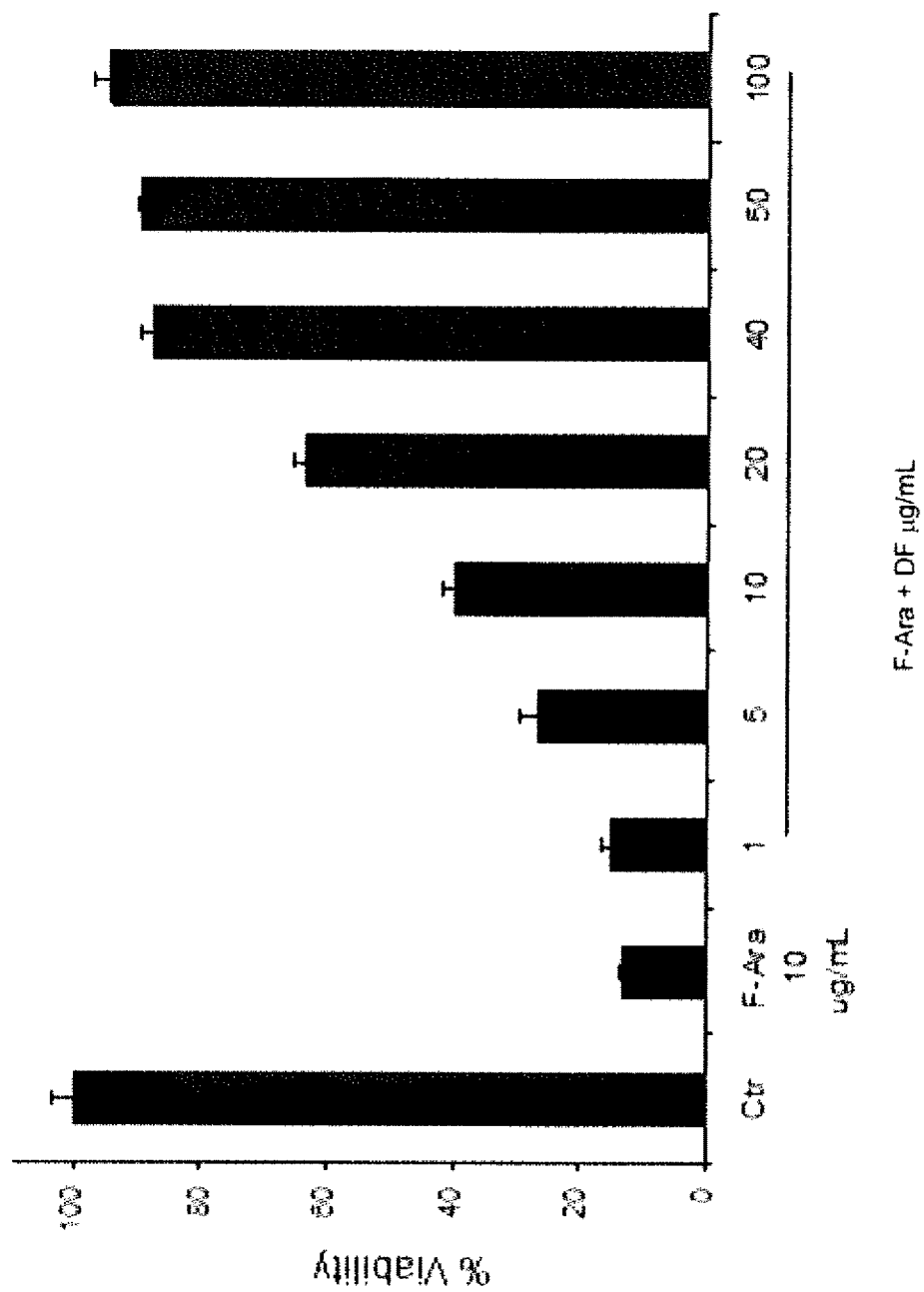
FIG. 6. Viability of SK-HEP-1 cells incubated with fludarabine in the presence or absence of varying concentrations of defibrotide as measured by CCK-8 assay. SK-HEP-1 cells were incubated with fludarabine (F-Ara) at 10 µg/ml in the absence or presence of varying concentrations of defibrotide (DF) (1 µg/ml-100 µg/ml) for 72 hr and the viability of the cells was measured with the CCK-8 assay. Student t-test: p<0.01, F-Ara 10 µg/ml vs. control (Ctr) and for cells treated with DF at >1 µg/ml vs. F-Ara 10 µg/ml.

SK-HEP-1 cells were grown and expanded according to the above mentioned procedure. The cells at a cell density of about 50,000 cells/ml were plated in a poly-D-lysine coated 96-well microplate. The cytotoxic agent was fludarabine at a concentration of 10 µg/ml. Defibrotide was added to each well at a concentration of 100, 50, 40, 20, 10, 5 or 1 µg/ml. Each treatment condition was run in 4 replicate wells. The viability was assessed after 72 hours of incubation with the CCK-8 assay kit. Defibrotide produced a dose-dependent cell protection effect from fludarabine-induced cytotoxicity with greater than 80% of the cells surviving with concentrations of defibrotide of 40 µg/ml or greater (FIG. 6).

Example 7

The present example shows the application of the cell-based protection assay for the assessment of the potency of a defibrotide sample of unknown biological activity.

SK-HEP-1 cells were grown and expanded according to the above mentioned procedure. The cells were plated at a cell density of about 50,000 cells/ml in poly-D-lysine-coated microplates. The cytotoxic agent was fludarabine at a concentration of 10 µg/ml. The defibrotide reference standard and the defibrotide test sample were added to separate wells at a concentration of 80, 40, 20, 10, 5, 2.5, or 1.25 µg/ml. Four replicate wells were run for each treatment condition. The viability of the cells was assessed with the CCK-8 assay kit after 72 hours of incubation.

The absorbances measured for the defibrotide reference standard samples and the defibrotide test samples were submitted to a 4-parameter logistic function analysis. That is, the dose-response of the reference and sample defibrotide curves can be described by a 4-parameter logistic function:

$$\upsilon = \delta + \frac{\alpha - \beta}{1 + e^{-\beta(x-\gamma)}}$$

Figure 7:
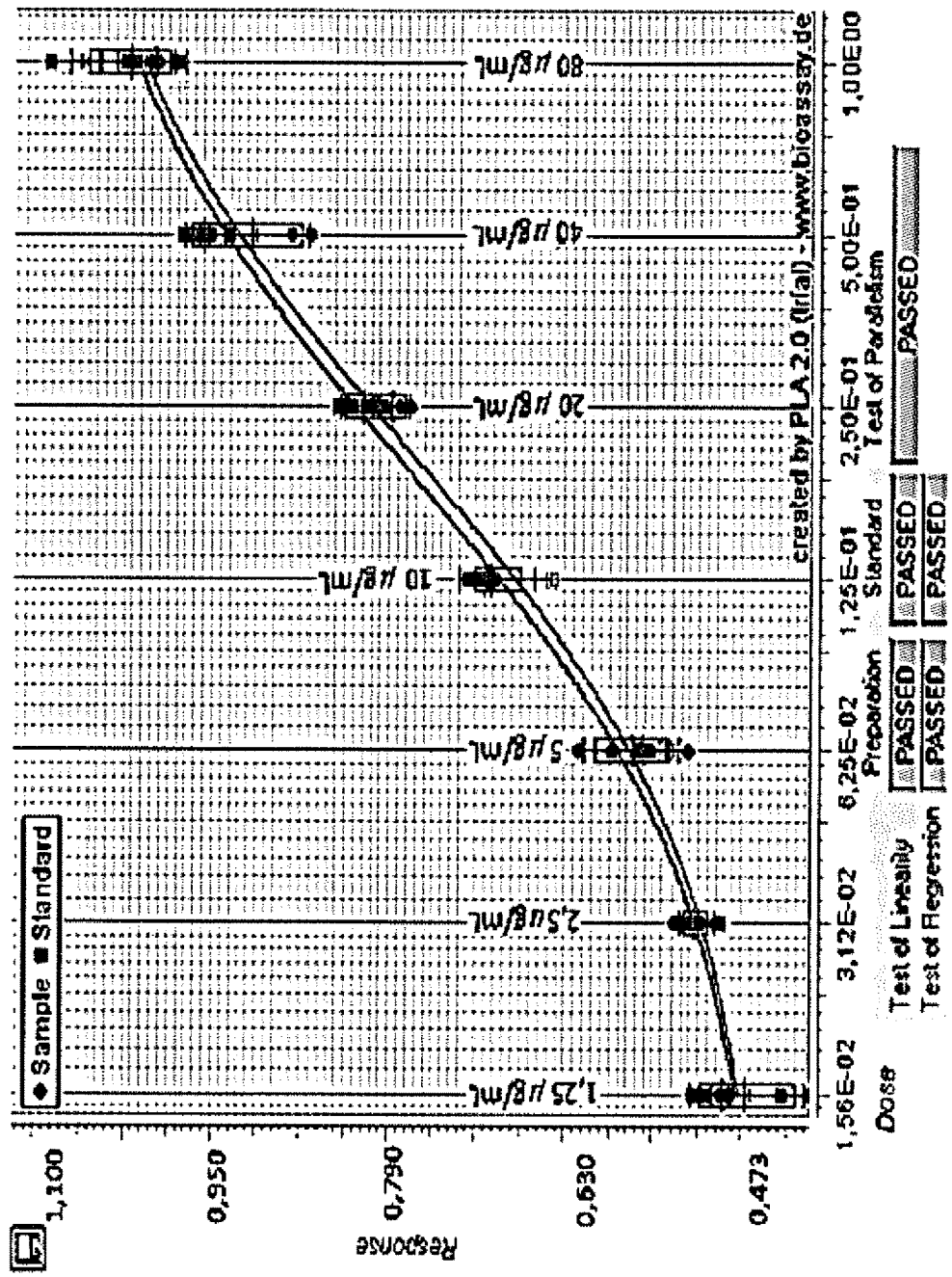
FIG. 7. Assessment of the potency ratio between a standardized Reference defibrotide sample (standard) and a sample of defibrotide of unknown biological activity. SK-HEP-1 cells were exposed to 6 serial dilutions (1:2) of standard and sample defibrotide to give concentration of 80, 40, 20, 10, 5, 2.5 and 1.25 µg/ml in the presence of fludarabine (F-Ara) (10 µg/ml). Each concentration of the standard and the sample consisted of 4 replicates. After 72 hr incubation at 37° C., the viability of the cells was measured with the CCK-8 assay. The absorbance measurements were submitted to statistical analysis for sample potency determination (4-parameter logistic analysis).

Where, $\upsilon$ is the response, $\alpha$ is the upper asymptote, $\delta$ is the lower asymptote, $\beta$ is the slope-factor, and $\gamma$ is the horizontal location of the sample curve on the x axis. The potency of the defibrotide test sample was determined by calculating a potency ratio against the defibrotide reference standard. The potency ratio for the defibrotide test sample was 1.157 (FIG. 7).

Example 8

The present example evaluates the precision of the defibrotide potency determinations of the cell-based protection assay. The potency of the same defibrotide test sample was measured, against a defibrotide reference standard, in repeated assays by different analysts, using different batches of qualified medium, cell batches and pipetting devices.

SK-HEP-1 cells were grown and expanded according to the above mentioned procedure. The cells were plated at a cell density of about 50,000 cells/ml in poly-D-lysine-coated microplates. The cytotoxic agent was fludarabine at a concentration of 10 µg/ml. The defibrotide reference standard and the defibrotide test sample were added to separate wells at the same series of concentrations as described in Example 7. Four replicate wells were run for each experimental condition. The viability of the cells was assessed with the CCK-8 assay kit after 72 hours of incubation.

The absorbances measured for each well in each assay run were subject to a 4-parameter logistic function analysis and potency ratio against the defibrotide reference standard was calculated as described in Example 7. The potency ratio of the same defibrotide test sample in each assay run is shown in Table 2. From the potency measurements by different analysts under the variable conditions shown in Table 2, the assay has a high a precision (% relative standard deviation of 7.8) and a low bias of <3%.

TABLE 2

Precision of the assay is demonstrated by analysing the same test sample, against the defibrotide standard, in different assay runs, on different days and cells of a different passage number.

| Assay run | Day | Analyst | Cell passage number | Pipetting device set | Measured Potency |
|---|---|---|---|---|---|
| 1 | 1 | 1 | 1 | #1 | 0.901 |
| 2 | 2 | 1 | 1 | #2 | 0.998 |
| 3 | 2 | 1 | 2 | #1 | 0.937 |
| 4 | 2 | 1 | 1 | #1 | 1.087 |
| 5 | 2 | 1 | 2 | #2 | 1.011 |
| 6 | 3 | 2 | 1 | #1 | 1.057 |
| 7 | 3 | 2 | 2 | #1 | 1.068 |
| 8 | 3 | 1 | 2 | #1 | 0.944 |
| 9 | 4 | 2 | 1 | #1 | 0.971 |
| 10 | 4 | 2 | 2 | #1 | 1.11 |
| 11 | 5 | 2 | 1 | #2 | 1.135 |
| 12 | 5 | 2 | 2 | #2 | 1.13 |

Example 9

The present example shows a comparison of the potency as determined by the cell-based protection assay for three different batches of defibrotide and a defibrotide reference standard.

SK-HEP-1 cells were grown and expanded according to the above mentioned procedure. The cells were plated at a cell density of about 50,000 cells/ml in poly-D-lysine-coated microplates. The cytotoxic agent was fludarabine at a concentration of 10 µg/ml. The defibrotide reference standard and the different defibrotide test samples from three separate batches were added to separate wells at a concentration of 80, 40, 20, 10, 5, 2.5, or 1.25 µg/ml. Four replicate wells were run for each experimental condition. The viability of the cells was assessed with the CCK-8 assay kit after 72 hours of incubation.

The absorbances measured for each well were submitted to a 4-parameter logistic function analysis and the potency ratio for each batch of defibrotide was calculated as described in Example 7. The potency ratio relative to the defibrotide standard, of each of the defibrotide test samples from the three batches is shown in Table 3.

TABLE 3

Potency ratios for three different batches of defibrotide analysed against a defibrotide reference standard.

| Defibrotide batch | Linearity, Regression and Parallelism tests | 95% Confidence Interval | Potency |
|---|---|---|---|
| 1080030021 | Passed | 0.823-0.989 | 0.902 |
| 1080060117 | Passed | 0.697-0.889 | 0.787 |
| 1080010016 | Passed | 1.116-1.725 | 1.387 |

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

Example 10

It would be useful to add experimental data directly comparing the method of the present invention with that of D3.

The invention claimed is:

1. A method of assessing the potency of a sample batch of defibrotide comprising:
   growing mammalian cells in culture;
   incubating the cells with a solution containing at least one cytotoxic agent and at least one concentration of defibrotide from the sample batch;
   measuring the viability of the cells after an incubation period;
   comparing the cell viability to the cell viability for a reference batch of defibrotide; and
   calculating the potency of the sample batch of defibrotide based on the comparison.

2. The method of claim 1, wherein the cells are incubated with the cytotoxic agent and at least four different concentrations of defibrotide from the sample batch, and wherein the cell viability is determined for each of the concentrations to create a dose-response curve.

3. The method of claim 1 wherein the cell viability measured for the sample batch of defibrotide is compared to a calibration curve obtained from cell viability measurements with the reference batch of defibrotide.

4. The method of claim 1, wherein calculating the potency of the defibrotide sample batch comprises determining a potency ratio relative to the potency of a reference batch of defibrotide.

5. The method of claim 1, wherein the mammalian cells are human endothelial cells, human epithelial cells, human liver sinusoidal endothelial cells, or human microvascular endothelial cells.

6. The method of claim 1, wherein the mammalian cells are present at a density of about $5 \times 10^4$ cells/ml to about $5 \times 10^5$ cells/ml.

7. The method of claim 1, wherein the cytotoxic agent is fludarabine, 9-beta-D-arabinofuranosyl-2-fluoroadenine (F-Ara-A), or doxorubicin.

8. The method of claim 7, wherein fludarabine or F-Ara-A is present in the solution at a concentration of about 10 µg/ml to about 50 µg/ml or wherein doxorubicin is present in the solution at a concentration of about 0.1 µg/ml to about 10 µg/ml.

9. The method of claim 1, wherein the at least one concentration of defibrotide from the sample batch is in the range of about 1 µg/ml to about 100 µg/ml.

10. The method of claim 1, wherein the incubation period is at least 24 hours, at least 48 hours, or at least 72 hours.

11. The method of claim 1, wherein measuring cell viability comprises performing a colorimetric assay based on the reduction of tetrazolium dyes.

12. The method of claim 11, wherein the tetrazolium dye is 3-(4,5-dimethylthiazol-2-yl)-2,5-diphenyltetrazolium bromide or 2-(2-methoxy-4-nitrophenyl)-3-(4-nitrophenyl)-5-(2,4-disulfophenyl)-2H-tetrazolium.

13. The method of claim 1, wherein measuring cell viability comprises measuring the absorbance of the solution following incubation with the cells.

14. The method of claim 1, wherein the sample batch of defibrotide is extracted from bovine tissue or porcine tissue.

15. A method of assessing the potency of a sample batch of defibrotide comprising:
   growing mammalian cells in culture in a multi-well microtiter plate;
   incubating the cells with a solution containing at least one cytotoxic agent and at least four different concentrations of defibrotide from the sample batch;
   collecting dose response data points simultaneously;
   measuring the viability of the cells after an incubation period;
   comparing the cell viability to the cell viability for a reference batch of defibrotide; and
   calculating the potency of the sample batch of defibrotide based on the comparison.

16. The method of claim 15, wherein the cells are incubated with a solution containing defibrotide at a concentration between 1.25 to 80 µg/mL.

17. The method of claim 15, wherein the cell viability is determined for each of the concentrations to create a dose-response curve.

18. The method of claim 15, wherein the cytotoxic agent fludarabine or F-Ara-A is present in the solution at a concentration of about 10 µg/ml.

19. The method of claim 15, wherein the multi-well microtiter plate is a 96-well plate.

20. The method of claim 15, wherein at least 3 replicates of incubating the cells with a solution containing at least one cytotoxic agent and at least four different concentrations of defibrotide from the sample batch is performed.

* * * * *